(12) United States Patent
Keusenkothen et al.

(10) Patent No.: US 9,708,231 B2
(45) Date of Patent: Jul. 18, 2017

(54) METHOD AND APPARATUS FOR CONVERTING HYDROCARBONS INTO OLEFINS USING HYDROPROCESSING AND THERMAL PYROLYSIS

(75) Inventors: Paul F. Keusenkothen, Houston, TX (US); Frank Hershkowitz, Basking Ridge, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 268 days.

(21) Appl. No.: 13/994,476

(22) PCT Filed: Dec. 20, 2011

(86) PCT No.: PCT/US2011/066152
§ 371 (c)(1),
(2), (4) Date: Sep. 18, 2013

(87) PCT Pub. No.: WO2012/099671
PCT Pub. Date: Jul. 26, 2012

(65) Prior Publication Data
US 2015/0166430 A1    Jun. 18, 2015

Related U.S. Application Data

(60) Provisional application No. 61/434,413, filed on Jan. 19, 2011, provisional application No. 61/434,415, (Continued)

(30) Foreign Application Priority Data

Mar. 31, 2011  (EP) ..................................... 11160755

(51) Int. Cl.
*C07C 4/04*     (2006.01)
*C10G 47/02*    (2006.01)
(Continued)

(52) U.S. Cl.
CPC .............. *C07C 4/04* (2013.01); *B01J 19/245* (2013.01); *C07C 5/09* (2013.01); *C08F 110/02* (2013.01); *C10G 47/02* (2013.01); *B01J 2219/24* (2013.01)

(58) Field of Classification Search
CPC ... C07C 4/04; C07C 5/09; C07C 13/18; C08F 110/02; C10G 47/02; C10G 2400/20; B01J 19/245; B01J 2219/24
(Continued)

(56) References Cited

U.S. PATENT DOCUMENTS

| | | | |
|---|---|---|---|
| 1,134,677 | A | 4/1915 | Heinemann |
| 1,860,624 | A | 5/1932 | Sauerwein |

(Continued)

FOREIGN PATENT DOCUMENTS

| | | |
|---|---|---|
| BE | 722895 | 10/1968 |
| DE | 875198 | 4/1953 |

(Continued)

OTHER PUBLICATIONS

Energy Fuels, 2007, 21(2), pp. 640-645.
(Continued)

*Primary Examiner* — In Suk Bullock
*Assistant Examiner* — Aaron Pierpont

(57) ABSTRACT

An apparatus and method are provided for processing hydrocarbon feeds. The method may contact hydrogen ($H_2$) and a hydrocarbon feed containing ≥10 wt % resid in the hydrocarbon feed with a catalyst to form a hydroprocessed product. Then, a pyrolysis feed derived from the hydroprocessed product is exposed at high-severity thermal pyrolysis operating conditions to produce a reactor product that comprises ethylene and acetylene. Further, at least a portion of the hydrogen ($H_2$) may be separated from the reactor product,
(Continued)

wherein the hydrogen (H₂) contacting the catalyst includes at least a portion of the separated hydrogen (H₂).

16 Claims, 9 Drawing Sheets

Related U.S. Application Data filed on Jan. 19, 2011, provisional application No. 61/434,411, filed on Jan. 19, 2011, provisional application No. 61/434,417, filed on Jan. 19, 2011, provisional application No. 61/434,419, filed on Jan. 19, 2011, provisional application No. 61/434,409, filed on Jan. 19, 2011, provisional application No. 61/434,410, filed on Jan. 19, 2011, provisional application No. 61/481,999, filed on May 3, 2011, provisional application No. 61/500,854, filed on Jun. 24, 2011, provisional application No. 61/504,611, filed on Jul. 5, 2011.

(51) Int. Cl.
  *C07C 5/09* (2006.01)
  *B01J 19/24* (2006.01)
  *C08F 110/02* (2006.01)

(58) Field of Classification Search
  USPC .................................. 526/75; 585/256, 539
  See application file for complete search history.

(56) References Cited

U.S. PATENT DOCUMENTS

| | | | |
|---|---|---|---|
| 2,319,679 A | 5/1943 | Hasche et al. | |
| 2,678,339 A | 5/1954 | Harris | |
| 2,692,819 A | 10/1954 | Hasche et al. | |
| 2,885,455 A * | 5/1959 | Hennig .................. | C07B 61/00 422/218 |
| 2,908,625 A * | 10/1959 | Korpi ..................... | C07C 11/02 208/101 |
| 3,024,094 A * | 3/1962 | Coberly .................. | C07C 4/04 422/218 |
| 3,093,697 A | 6/1963 | Kasbohm et al. | |
| 3,156,733 A | 11/1964 | Happel et al. | |
| 3,242,223 A | 3/1966 | Nonnenmacher et al. | |
| 3,268,615 A * | 8/1966 | Keenan, III ............ | C07C 4/04 585/635 |
| 3,419,632 A | 12/1968 | Sogawa et al. | |
| 3,617,495 A | 11/1971 | Zimmerman, Jr. et al. | |
| 3,644,555 A | 2/1972 | Nagy et al. | |
| 3,839,484 A | 10/1974 | Zimmerman, Jr. et al. | |
| 4,274,841 A | 6/1981 | Andresen et al. | |
| 5,675,041 A | 10/1997 | Kiss et al. | |
| 5,856,592 A | 1/1999 | Hagen | |
| 6,049,011 A | 4/2000 | Kiss et al. | |
| 6,121,503 A | 9/2000 | Janssen et al. | |
| 6,177,600 B1 | 1/2001 | Netzer | |
| 6,210,561 B1 | 4/2001 | Bradow et al. | |
| 6,307,093 B1 | 10/2001 | Godwin et al. | |
| 6,578,378 B2 | 6/2003 | Kaiser et al. | |
| 7,045,670 B2 | 5/2006 | Johnson et al. | |
| 7,115,789 B2 | 10/2006 | Kuechler et al. | |
| 7,119,240 B2 | 10/2006 | Hall et al. | |
| 7,138,047 B2 | 11/2006 | Stell et al. | |
| 7,208,647 B2 | 4/2007 | Peterson et al. | |
| 7,491,250 B2 | 2/2009 | Hershkowitz et al. | |
| 7,815,873 B2 | 10/2010 | Sankaranarayanan et al. | |
| 7,846,401 B2 | 12/2010 | Hershkowitz et al. | |
| 7,943,808 B2 | 5/2011 | Hershkowitz et al. | |
| 8,158,837 B2 | 4/2012 | Mamadov et al. | |
| 8,440,070 B2 | 5/2013 | Keusenkothen | |
| 2002/0000085 A1 | 1/2002 | Hall et al. | |
| 2002/0098430 A1 | 7/2002 | Kawamura et al. | |
| 2004/0002553 A1 | 1/2004 | Hall et al. | |
| 2004/0192982 A1 | 9/2004 | Kuechler et al. | |
| 2005/0065392 A1 * | 3/2005 | Peterson .................. | C07C 2/78 585/324 |
| 2007/0090018 A1 | 4/2007 | Keusenkothen et al. | |
| 2007/0090019 A1 * | 4/2007 | Keusenkothen et al. ..... | 208/106 |
| 2007/0090020 A1 | 4/2007 | Buchanan et al. | |
| 2007/0191664 A1 * | 8/2007 | Hershkowitz et al. ....... | 585/539 |
| 2008/0142049 A1 | 6/2008 | Onishi et al. | |
| 2008/0300438 A1 | 12/2008 | Keusenkothen et al. | |
| 2010/0130803 A1 | 5/2010 | Keusenkothen et al. | |
| 2010/0292523 A1 | 11/2010 | Hershkowitz et al. | |

FOREIGN PATENT DOCUMENTS

| | | |
|---|---|---|
| DE | 1270537 | 6/1968 |
| DE | 2354217 | 5/1975 |
| EP | 1288182 | 3/2003 |
| EP | 1741691 | 1/2007 |
| EP | 2022772 | 2/2009 |
| GB | 795688 | 5/1958 |
| GB | 834419 | 5/1960 |
| GB | 846679 | 8/1960 |
| GB | 1007423 | 10/1965 |
| GB | 1090983 | 11/1967 |
| WO | 2005/097948 | 10/2005 |
| WO | 2011/008389 | 1/2011 |
| WO | 2012/099679 | 7/2013 |

OTHER PUBLICATIONS

Watt, L., "The Production of Acetlene from Methane by Partial Oxidation", Thesis University OG British Columbia, Sep. 1, 1951, pp. 1-50.

SRI Consulting Process Economics Program "Acetylene" Report 16 (1966) and 16A (1982).

* cited by examiner

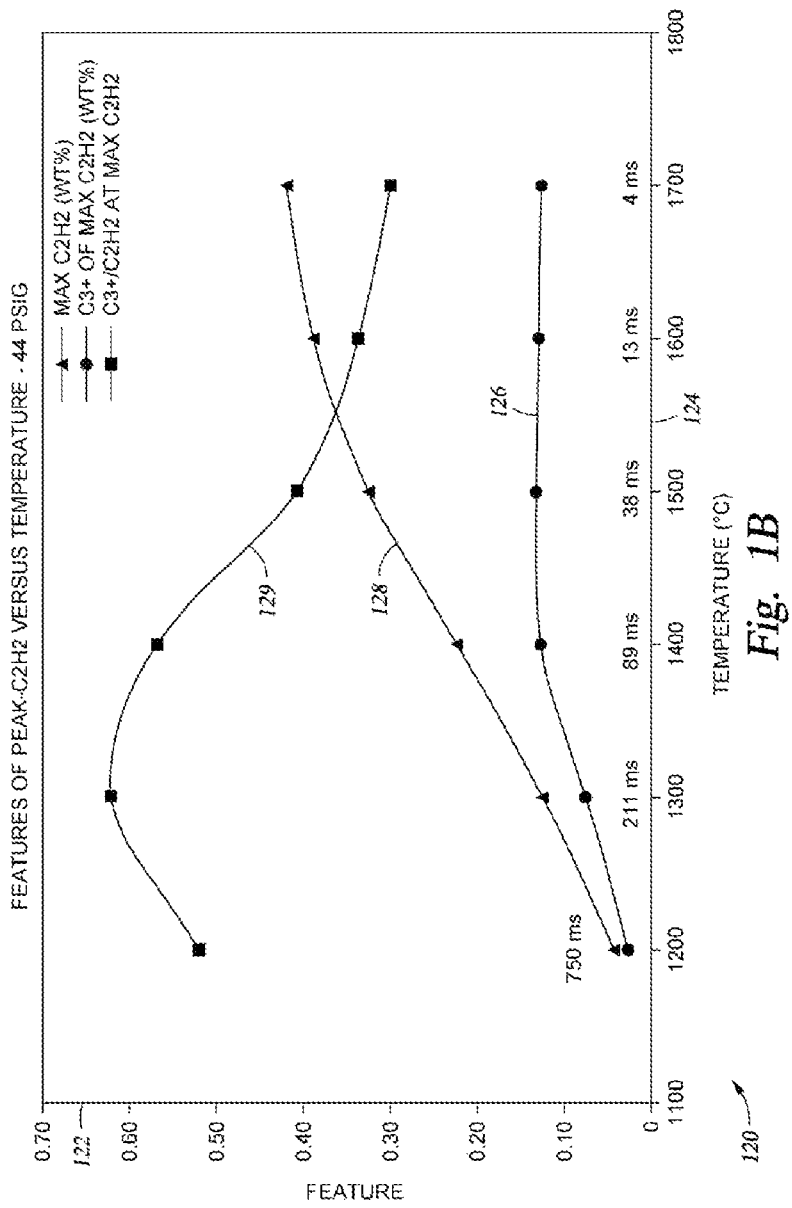

METHOD AND APPARATUS FOR CONVERTING HYDROCARBONS INTO OLEFINS USING HYDROPROCESSING AND THERMAL PYROLYSIS

CROSS-REFERENCE TO RELATED APPLICATIONS

This application claims priority from (i) U.S. Provisional Application Ser. No. 61/434,415, filed Jan. 19, 2011, EP Application No. 11160755.2, filed on Mar. 31, 2011, and PCT/US2011/066152, filed Dec. 20, 2011; (ii) U.S. Provisional Application Ser. No. 61/434,409, filed Jan. 19, 2011, and PCT/US2011/066216, filed Dec. 20, 2011; (iii) U.S. Provisional Application Ser. No. 61/434,410, filed Jan. 19, 2011, and PCT/US2011/066202, filed Dec. 20, 2011; (iv) U.S. Provisional Application Ser. No. 61/434,411, filed Jan. 19, 2011, and PCT/US2011/066210, filed Dec. 20, 2011; (v) U.S. Provisional Application Ser. No. 61/434,413, filed Jan. 19, 2011, and PCT/US2011/066196, filed Dec. 20, 2011; (vi) U.S. Provisional Application Ser. No. 61/434,417, filed Jan. 19, 2011, and PCT/US2011/066186, filed Dec. 20, 2011; (vii) U.S. Provisional Application Ser. No. 61/434,419, filed Jan. 19, 2011, and PCT/US2011/066206, filed Dec. 20, 2011; (viii) U.S. Provisional Application Ser. No. 61/481,999, filed May 3, 2011, and PCT/US2011/066180, filed Dec. 20, 2011; (ix) U.S. Provisional Application Ser. No. 61/500,854, filed Jun. 24, 2011, and PCT/US2011/066174, filed Dec. 20, 2011; and (x) U.S. Provisional Application Ser. No. 61/504,611, filed Jul. 5, 2011, and PCT/US2011/066165, filed Dec. 20, 2011, the contents of each of which are incorporated by reference in their entirety.

FIELD

The present techniques relate to a method for converting hydrocarbons into unsaturated products, such as ethylene, which may be optionally polymerized into the other products, such as polyolefins. Further, the present techniques relate to an apparatus useful for the process, which enhances the conversion of hydrocarbons into olefins and other products.

BACKGROUND

The oil, gas and petrochemical industry desires to efficiently obtain hydrocarbons and process the hydrocarbons to produce desired products. Refining processes involve upgrading, converting or separating hydrocarbons (e.g., crude oil) into different streams, such as gases, light naphtha, heavy naphtha, kerosene, diesel, atmospheric gas oil, asphalt, petroleum coke and heavy hydrocarbons or fuel oil. Similarly, natural gas may be converted into industrial fuel gas, liquefied natural gas (LNG), ethane, propane, liquefied petroleum gas (LPG), and natural gas liquids (NGLs). The oil and gas processes are also often integrated with petrochemical systems to convert refinery streams into chemical products, such as ethylene, propylene or polyolefins.

To convert hydrocarbon feeds into petrochemical or basic chemicals, chemical conversion processes may be utilized. These processes typically involve using thermal or catalytic reactors or furnaces to produce reactive hydrocarbon products, such as acetylene, ethylene or propylene in different proportions. As an example, steam cracking reactors are commonly utilized to convert the hydrocarbon feed into ethylene and acetylene, which may be further processed into various chemical products. The steam cracking reactors are utilized because they provide feed flexibility by being able to utilize gas (e.g., ethane) and liquid (e.g., naphtha through gas oils) feeds.

Historically, the oil and gas refineries utilize the higher value distillates from the hydrocarbon feed, which are typically fungible fuels, such as mogas, natural gas and diesel. As a result, the petrochemical refineries utilize the remaining fractions, such as ethane, propane, naphtha and virgin gas oil, in their processes. However, few chemical conversion processes are able to directly employ natural gas or the lower value refinery feeds, such as aromatic gas oils or fuel oils. As such, there is a need for a process that can produce ethylene and acetylene from different feeds, such as advantaged feeds (e.g., aromatic fuel oils) and/or feeds having lower hydrogen content, for example.

To process these feeds, high-severity operating conditions (e.g., more severe operating conditions, such as higher temperatures) are generally used to produce products having a higher value than the feed. High-severity operating conditions enable methane cracking and aromatic ring cracking, which do not occur at appreciable rates at typical low-severity conditions (e.g., conventional steam cracking conditions). At high-severity operating conditions, the primary products of thermal chemical conversion processes are acetylene and ethylene along with hydrogen ($H_2$) and coke, which may vary in proportion depending on the temperatures, pressures, residence times and feed type utilized in the conversion process. Although high-severity operating conditions typically yield predominately acetylene, acetylene may be further converted to ethylene and ultimately polyethylene or other derivatives using conventional technology. High-severity and low-severity conversion processes are typically based on different pyrolysis reactors, which may include pyrolysis alone or integrated with combustion chemistry. That is, the reactors may include pyrolysis chemistry (e.g., thermochemical decomposition of feed at elevated temperatures in the absence of oxygen) alone or in combination with combustion chemistry (i.e., exothermic chemical reactions between a feed and an oxidant). These pyrolysis reactors can be divided into different types: partial combustion that burns part of the pyrolysis feed, indirect combustion that involves contacting the pyrolysis feed with combustion products, arc process that generate the electric arc or plasma to crack the pyrolysis feed, and thermal pyrolysis. Each of these pyrolysis types differs in the means of generating and transferring the heat for the pyrolysis, but may be broadly characterized as low-severity or high-severity.

Thermal pyrolysis reactors involve heating a solid material (e.g., by combustion) and using the heated solid material to crack the pyrolysis feed. In the thermal pyrolysis processes, the combustion products are typically maintained separate from the reactor effluent. This pyrolysis technique involves different reactors, such as a furnace (e.g., as used in steam cracking), a regenerative reactor (e.g., as used in the Wulff process) and others. For instance, thermal pyrolysis is generally described in various references, such as U.S. Pat. Nos. 7,138,047 and 7,119,240. U.S. Pat. No. 7,119,240 describes an exemplary process for the conversion of natural gas into ethylene. In this process, natural gas is cracked in a furnace, actively quenched, and processed in a reactor to produce ethylene. As another example, U.S. Pat. No. 7,138,047 describes a steam cracking process that mixes a hydrocarbon feed with a dilution steam, flashing the mixture, and vaporizing a portion of the mixture in a pyrolysis reactor. In the process, the pyrolysis feed is passed through tubes in the radiant section of a thermal pyrolysis reactor to crack the pyrolysis feed without contaminating it with combustion products. However, due to the nature of a tubular (metal) furnace, steam cracking is limited to effective cracking temperatures of below 1000° C. and residence times of greater than or equal to (≥) 100 milliseconds (ms), which do not effectively convert either methane or aromatics, thereby limiting the feedstock selection. In addition, energy or furnace heat not used in cracking is partially lost in the furnace flue gas or in the quench, as products are quickly cooled to stop undesired reactions.

The "Wulff" reactor, as described in the IHS, SRI Consulting's Process Economics Program "Acetylene" Report Number 16 (1966) and 16A (1982) along with U.S. Pat. Nos. 2,319,679; 2,678,339; 2,692,819; 3,024,094; 3,093,697 and 3,839,484, uses a reverse-flow pyrolysis reactor, which is operated at temperatures of less than (<) 1400° C., to produce olefins and alkynes, such as acetylene. The pyrolysis feed is heated by refractories which have previously been heated by combustion reactions. The pyrolysis feed is cracked, and then further cooled outside of the reactor. The relatively slow quenching is a characteristic of the Wulff process that leads to coke and soot formation from using inefficient indirect heat transfer (e.g., from checker brick). Coke formation in the reactor provides fuel during the combustion cycle and excess coke or soot may be alleviated by using a light feed, i.e., a hydrocarbon containing a high proportion of hydrogen. However, because the indirect heat transfer limits the rate of heat input in the Wulff process, certain pyrolysis feeds, such as methane, may not be economically processed, which limits the feed flexibility for this process.

Further, while pyrolysis regenerative reactors have been used commercially, these reactors are not widely used for the conversion of certain feeds (e.g., natural gas or fuel oils) into acetylene or ethylene. That is, the inefficient refractories limit heat transfer (both for adding heat necessary for pyrolysis and for removing heat necessary for quenching). As a result, the Wulff reactors typically involve cracking temperatures below 1400° C. and involve the use of more expensive feeds, such as ethane, propane and naphtha. In addition, the poor heat transfer limits lead to greater soot generation resulting in poorer selectivity to desired products.

U.S. patent application Ser. No. 12/814,178 describes a process for preparing a resid-containing hydrocarbon feedstock for use in a regenerative pyrolysis reactor. The reference describes feeding a resid-containing hydrocarbon feedstock to and thermally converting in a visbreaker or coker of a resid having a boiling point of at least 565° C. to form a vapor phase containing cracked hydrocarbons. The converted feed is separated to a vapor phase from remaining non-volatiles and the separated vapor phase is cracked in a regenerative pyrolysis reactor. Visbreakers and cokers, however, are limited in the 565° C. conversion and yield either low value visbreaker tar or coke as a byproduct. Higher conversions are impractical due to increased fouling during thermal conversion.

Moreover, various references describe that the reverse flow reactor is not feasible for converting methane to ethylene. In a comparison of the known acetylene conversion technologies, including the partial combustion, indirect combustion, arc processes, and thermal pyrolysis, the regenerative reactors are considered infeasible for methane to ethylene conversion due to the lower attainable temperatures in the Wulff process. That is, the Wulff process, which has checker bricks or refractory tiles within the reactor, is unable to withstand the constant temperature changes inherent in the process. Further, certain of the references describes that partial oxidation of natural gas to acetylene with heat recovery is the most economical process. These references dismiss the use or lighter feeds, such as methane, because it can not be used economically. As such, the use of a reverse flow reactor is not taught as being possible for various reasons.

Although pyrolysis reactors may be used to convert hydrocarbons into useful products, such as acetylene and ethylene, improved reactions are desired which can make use of a broader range of feeds, such as lower hydrogen content feeds. The use of hydrotreating units to upgrade feed for use in a low-severity pyrolysis reactor has been performed. For example, U.S. Pat. Nos. 3,839,484 and 6,210, 561 and U.S. Patent App. Pub. Nos. 2007/0090020; 2007/ 0090019; and 2007/0090018 are examples of hydrotreating processes that are used to upgrade the feed. However, such hydrotreating units have to substantially convert aromatic hydrocarbons to saturated hydrocarbons for those hydrocarbons to be cracked by the low-severity pyrolysis reactor. The conversion of aromatics to saturates is an expensive process because the cost of hydrogen and the required pressure associated with such equipment. In contrast, hydrotreating merely for molecular weight reduction may be performed at lower pressures, consumes less hydrogen and may be less costly. Accordingly, it is desirable to have a process that may convert high-boiling and low hydrogen content hydrocarbon feeds to high-value petrochemicals, such as ethylene and propylene and their derivatives without the need to saturate aromatic rings. Accordingly, it is desirable to provide a process that converts hydrocarbon feeds having lower hydrogen content into ethylene and/or propylene in an enhanced manner.

SUMMARY

A method for processing hydrocarbons comprising: (i) contacting hydrogen ($H_2$) and a hydrocarbon feed containing ≥10.0 wt % resid in the hydrocarbon feed with a catalyst to form a hydroprocessed product; (ii) exposing a pyrolysis feed derived from the hydroprocessed product at high-severity thermal pyrolysis operating conditions to produce a reactor product that comprises hydrogen, ethylene and acetylene; and (iii) separating at least a portion of the hydrogen ($H_2$) from the reactor product, wherein the hydrogen ($H_2$) contacting the catalyst comprises at least a portion of the separated hydrogen ($H_2$).

An apparatus for processing hydrocarbons comprising: (i) a hydroprocessing unit configured to contact hydrogen ($H_2$) and a hydrocarbon feed containing ≥10 wt % resid in the hydrocarbon feed with a catalyst to form a hydroprocessed product; (ii) a feed separation unit in fluid communication with the hydroprocessing unit and configured to receive the hydroprocessed product and separate a bottoms product from the hydroprocessed product; (iii) a thermal pyrolysis reactor in fluid communication with the feed separation unit configured to expose a pyrolysis feed derived from the hydroprocessed product at high-severity thermal pyrolysis operating conditions to produce a reactor product that comprises ethylene and acetylene; and (iv) a product separation unit in fluid communication with the thermal pyrolysis reactor and configured to separate hydrogen from at least a portion of the reactor product.

In one aspect, one or more embodiments of the present techniques provide a method for enhancing the conversion of hydrocarbon feedstocks, which may have a lower hydrogen content and poor volatility, into propylene and/or ethylene. In particular, the present techniques utilize a regenerative pyrolysis reactor system to convert these feeds into ethylene, propylene and other petrochemical products in an enhanced manner.

Further, in one or more embodiments, a method for converting hydrocarbons into olefins is described. The method comprises contacting hydrogen ($H_2$) and a hydrocarbon feed containing ≥10 wt % resid in the hydrocarbon feed with a catalyst to form a hydroprocessed product; exposing a pyrolysis feed derived from the hydroprocessed product at high-severity thermal pyrolysis operating conditions to produce a reactor product that comprises hydrogen, ethylene and acetylene; and separating at least a portion of the hydrogen ($H_2$) from the reactor product, wherein the hydrogen ($H_2$) contacting the catalyst comprises at least a portion of the separated hydrogen ($H_2$).

Further still, in one or more embodiments, an apparatus for processing hydrocarbons is described. The apparatus comprising a hydroprocessing unit, a feed separation unit, a thermal pyrolysis reactor and a product separation unit. The hydroprocessing unit is configured to contact hydrogen ($H_2$) and a hydrocarbon feed containing ≥10 wt % resid in the hydrocarbon feed with a catalyst to form a hydroprocessed product, while the feed separation unit is in fluid communication with the hydroprocessing unit and configured to receive the hydroprocessed product and separate a bottoms product from the hydroprocessed product. The thermal pyrolysis reactor is in fluid communication with the feed separation unit and is configured to expose a pyrolysis feed derived from the hydroprocessed product at high-severity thermal pyrolysis operating conditions to produce a reactor product that comprises ethylene and acetylene, while the product separation unit is in fluid communication with the thermal pyrolysis reactor and is configured to separate hydrogen from at least a portion of the reactor product.

Further, the method may involve operating the thermal pyrolysis reactor at operating conditions to provide a $C_{3+}$ to acetylene weight ratio ≤0.45, ≤0.4, or ≤0.3, while the ethylene to acetylene weight ratio is ≥0.1 or ≥0.5. Further still, the method may include mixing other fluids, such as hydrogen, with the reactor feed to form a pyrolysis feed having a hydrogen gas ($H_2$) to feed carbon molar ratio is 0.1 to 5. In addition, the method may involve operating the thermal pyrolysis reactor at operating conditions having pressures ≥4 pounds per square inch gauge (psig) (27 kilo Pascal gauge (kPag)), ≥15 psig (103 kPag), ≥36 psig (248 kilo Pascal (kPag)), or ≥44 psig (303 kPag) or ≥103 psig (710 kPag), but may be ≤300 psig (2068 kPag), or ≤163 psig (1124 kPag), or ≤150 psig (1034 kPag).

In other embodiments, the method may convert ≥20 wt % of the resid in the hydrocarbon feed to components lighter than resid; or ≥50 wt % of the resid in the hydrocarbon feed to components lighter than resid. Also, the method may include removing a portion of the combustible non-volatiles and the non-combustible non-volatiles from the hydroprocessed product to form the at least a portion of the hydroprocessed product having ≤5 wt % combustible non-volatiles and ≤2 ppmw non-combustible non-volatiles. The hydrocarbon feed may contain ≥1 wt % aromatic carbon content and wherein ≤20 wt % of the aromatic carbon in the hydrocarbon feed is converted to non-aromatic carbon.

In certain embodiments of the method or apparatus, the thermal pyrolysis reactor may be a regenerative reverse flow reactor. This reactor may include a reactor body, wherein the reactor body forms a reaction region within the reactor body; a packing material disposed at least partially within the reaction region; and one or more valve assemblies coupled to the reactor body and in flow communication with the reaction region and configured to control fluid flow of the at least a portion of the pyrolysis feed between a location external to the reactor body and within the reaction region. Further, the one or more valve assemblies may be poppet valve assemblies.

In certain embodiments of the method or apparatus, the high-severity operating conditions may include exposing the pyrolysis feed to a peak pyrolysis gas temperature from 1540.0° C. to 2200.0° C., and the residence time for the at least a portion of the pyrolysis feed within the thermal pyrolysis reactor is between 0.5 second and 0.001 second. In other embodiments, the high-severity operating conditions may include exposing the pyrolysis feed to a peak pyrolysis gas temperatures from 1600.0° C. to 1800.0° C., and the residence time for the at least a portion of the pyrolysis feed within the thermal pyrolysis reactor is between 0.5 second and 0.001 second. The method may involve a regenerative reactors having cycle time in a combustion step and a pyrolysis step in the reactor that is between 0.5 second to 30 seconds.

Moreover, in one or more embodiments, a product separation unit may be in fluid communication with units in the recovery stage and is configured to separate a hydrogen containing stream or hydrogen ($H_2$) from at least a portion of the reactor product or conversion product. At least a portion of the hydrogen ($H_2$) may be recycled to the hydroprocessing (e.g., hydrotreating unit) as the hydrogen ($H_2$) with other portions being combined with one of the hydroprocessed product, a combustion feed for use in the thermal pyrolysis reactor, an additional feed to the acetylene converter or a combination thereof.

BRIEF DESCRIPTION OF THE DRAWINGS

FIGS. 1A to 1F are diagrams of simulation results representing different ratios of reactor products produced at different temperatures and/or different pressures.

Figure 1A:
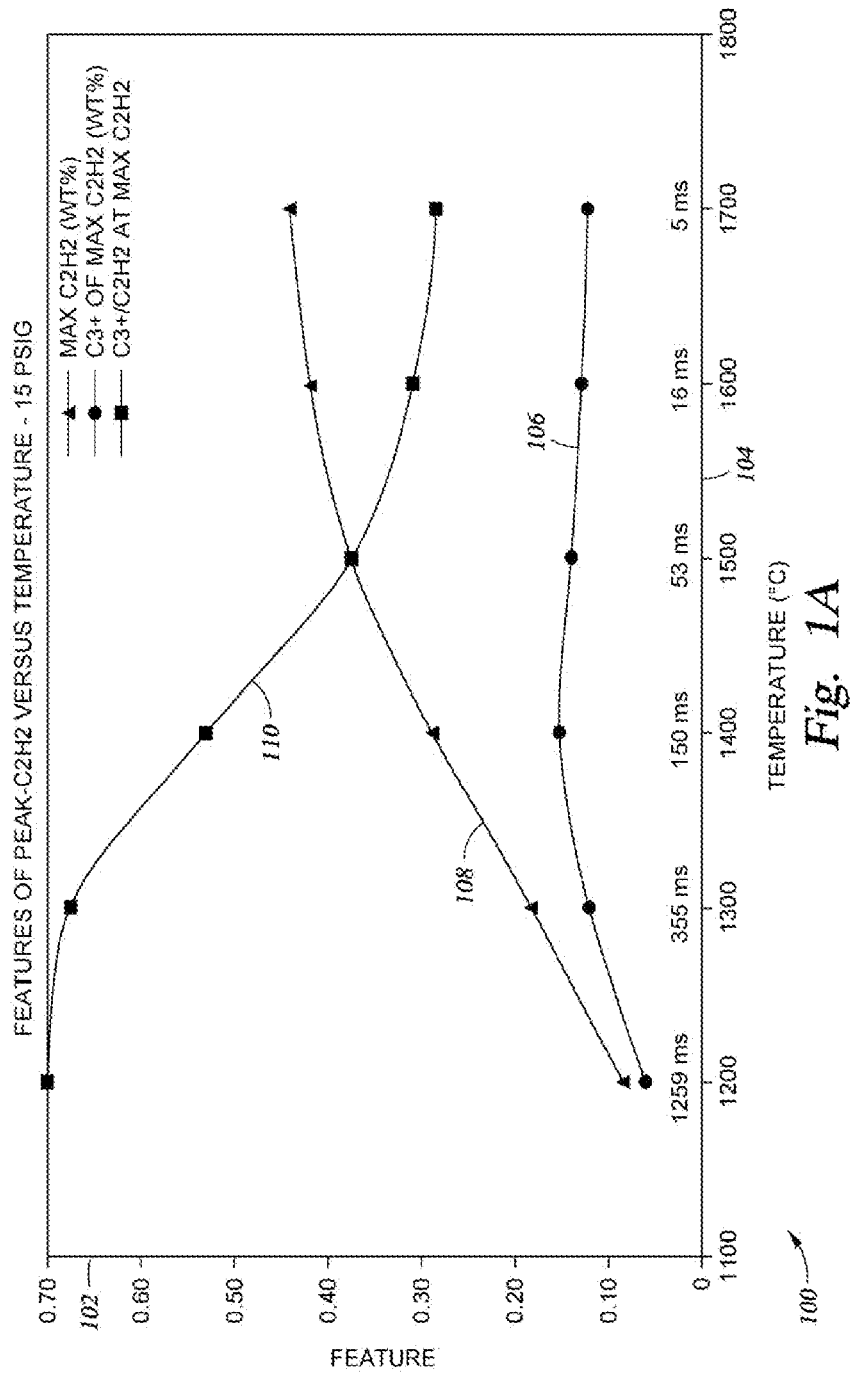

Although the invention is described in terms of a thermal pyrolysis process for producing acetylene and ethylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims.

DETAILED DESCRIPTION OF THE EMBODIMENTS

In contrast to conventional techniques, the present techniques provide an enhanced process for conversion of feed containing hydrocarbons, which may have lower hydrogen content and poor volatility, into acetylene and ethylene and optionally polyethylene. The present techniques utilize hydroprocessing along with thermal pyrolysis configured to expose at least a portion of the hydroprocessed feed (e.g., hydrotreated product) to higher temperatures than conventional steam cracking or Wulff liquid feed pyrolysis. These higher temperatures are utilized to crack feeds that are normally unreactive or react to low value products (e.g., degraded products) at lower temperatures. As a specific example, at temperatures ≥1200.0° C., methane and aromatic components are partially cracked to yield unsaturated $C_2$+ compounds, typically acetylenes and ethylene. At temperatures ≥1400.0° C. or preferably ≥1540.0° C., aromatics and methane may be cracked at high conversion levels, with selectivity levels ≥50 wt % to light gas products. That is, at atmospheric pressure, higher temperature also provides selectivity to enhance the yield of unsaturated $C_2$+ compounds (e.g., yield of ethylene and acetylene). For example, the ethylene to acetylene weight ratio (E/A) may be ≤0.10 or as low as 0.02 at atmospheric pressure. To further enhance the process, as noted below, higher pressure may be utilized to increase the E/A for certain operating conditions. The present techniques utilize hydroprocessing (e.g., a hydrotreating) along with a thermal pyrolysis to convert the hydrocarbon feed into acetylene and ethylene. The hydrocarbon feed may have a low hydrogen content that contains ≤about 15 wt % atomic hydrogen, ≤about 13 wt % atomic hydrogen, ≤about 11 wt % atomic hydrogen, or ≤about 8 wt % atomic hydrogen. The process may include blending the hydrotreated product with methane or other hydrogen rich feed to provide a blended mixture containing at least about 13 wt % atomic hydrogen. Then, the blended mixture may be separated from a bottoms product to remove solids, such as metals. Then, the remaining portion may be exposed to high-severity pyrolysis operating conditions, which may include a peak gas pyrolysis temperature ≥1400.0° C., ≥1500.0° C.; ≥1540.0° C., or ≥1650.0° C. Other operating conditions may include pressures ≥4 psig (27 kPag), ≥15 psig (103 kPag), ≥36 psig (248 kPag), ≥44 psig (303 kPag), or ≥150 psig (1034 kPag). Other aspects, such as the reactor product comprising a specific $C_{3+}$ to acetylene weight ratio or $C_{3+}$ to $C_2$ unsaturate ($C_2U$) weight ratio, may also be utilized to adjust the operating conditions, as discussed further below.

As noted above, pyrolyzing heavy, low hydrogen-content hydrocarbons normally yield high levels of dry gas (methane) and condensed aromatic rings. At low pyrolysis temperatures (≤1200° C.), dry gas and condensed aromatic rings are largely unreactive (i.e. do not crack); higher temperatures are need to convert methane and aromatics selectively to acetylene.

As a result, the present techniques provide a more efficient process to recover olefins by integrating hydroprocessing with thermal pyrolysis. For instance, present techniques provide flexibility in type of hydrocarbon feed utilized in the process. That is, any hydrocarbon feed provided may be hydrotreated and then a portion of the hydrotreated product may be exposed to high-severity operating conditions in a thermal pyrolysis reactor, which may include a broad range of lower value hydrocarbon feeds. To further explain the high-severity pyrolysis reactor and its associated products, various simulation results representing different ratios of reactor products produced at different temperatures and/or different pressures are provided. These simulations utilize certain feeds, such as methane, for simplicity, but the invention is not limited thereto. The benefits of this configuration provide a more efficient process to recover olefins by integrating hydroprocessing with high-severity thermal pyrolysis. These advantaged feeds, which do not typically react in at low-severity condition or react to lower value products, react in the process to provide $C_2U$. High-severity, as provided in the present process, converts at high levels aromatic containing and/or methane containing feeds to valuable $C_2$ products.

At any elevated temperature, hydrocarbon pyrolysis or hydropyrolysis produces acetylene at an intermediate residence time. As time continues, the hydrocarbons react further towards condensed species and eventually carbon (e.g., produce more coke). Thus, there is a maximum amount of acetylene, which is achieved at a specific residence time, and which is the optimum acetylene yield for a given temperature. The temperature and residence time of this maximum acetylene yield can be used to characterize thermal pyrolysis reactor performance at that temperature, in terms of the yield of $C_{3+}$ in relationship to the yield of acetylene. The yield of $C_{3+}$, as used herein, includes all $C_{3+}$ products of the pyrolysis feed, whether those products emerge from the reactor or remain within the reactor as coke. $C_{3+}$ includes, for example, products such as methyl acetylene, benzene and tar, and is specifically defined as including carbonaceous byproducts, such as coke. The maximum acetylene yield, the corresponding $C_{3+}$ yield and the acetylene to $C_{3+}$ weight ratio are described further in relation to temperature and residence time in FIGS. 1A and 1B and Table 1.

FIGS. 1A and 1B illustrate the simulation results for different weight ratios of reactor products produced at different temperatures from a methane feed. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen in a methane feed, and at 14.7 psig (101 kPag) pressure for diagram 100 and at 44 psig (303 kPag) pressure for diagram 120. All hydrocarbon products larger than $C_2$ are considered as $C_{3+}$ in this example and the product is the reaction product yield from the converted pyrolysis feed. In diagram 100, certain values for a maximum acetylene yield 108 in wt % of the product, and corresponding $C_{3+}$ yield 106 in weight percent (wt %) of the product and $C_{3+}$ to acetylene weight ratio 110 of the product are shown along the Y-axis 102 for various temperatures (in ° C.) along the X-axis 104. The $C_{3+}$ to acetylene weight ratio 110 has a peak between the temperatures of 1200° C. and 1400° C., which decreases at a slower rate as temperature increases from 1500° C. or 1540° C. Similarly, in diagram 120, certain values for a maximum acetylene yield 128 in wt % of the product, and corresponding $C_{3+}$ yield 126 in wt % of the product and $C_{3+}$ to acetylene weight ratio 129 of the product are shown along the Y-axis 122 for various temperatures (in ° C.) along the X-axis 124. The $C_{3+}$ to acetylene weight ratio 110 again has a peak within the range of 1300° C. to 1400° C., which decreases at a slower rate from 1500° C. or 1540° C. as the temperature increases. As such, operating conditions of the thermal pyrolysis reactor may be adjusted to enhance the acetylene yield for a pyrolysis feed.

This aspect is further described in Table 1, which includes simulation results for different ratios of reactor products produced at different temperatures from methane. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen (as $H_2$) in a methane feed, and at 14.7 psig (101 kPag) reactor pressure. Table 1 lists the results, such as composition of the pyrolysis product (weight percent of total pyrolysis product), for operations at temperatures between 1200° C. and 2200° C.:

TABLE 1

| | Temperature (° C.) | | | | | | | | |
|---|---|---|---|---|---|---|---|---|---|
| | 1200 | 1300 | 1400 | 1500 | 1540 | 1600 | 1650 | 1700 | 2200 |
| Max $C_2H_2$ (wt % of product) | 8.6% | 18.1% | 28.8% | 37.5% | 39.6% | 41.8% | 43.0% | 44.0% | 49.4% |
| Time of max $C_2H_2$ (sec) | 1.259 | 0.355 | 0.150 | 0.053 | 0.035 | 0.016 | 0.009 | 0.005 | 0.00006 |
| $C_3^+$ (wt % of product) | 6.0% | 12.2% | 15.3% | 14.0% | 13.7% | 12.9% | 12.6% | 12.3% | 12.9% |
| $C_3^+/C_2H_2$ | 0.699 | 0.673 | 0.530 | 0.372 | 0.346 | 0.308 | 0.293 | 0.281 | 0.261 |
| $C_2H_2$ /unit reactor volume (relative units) | 0.068 | 0.510 | 1.928 | 7.066 | 11.31 | 26.38 | 47.8 | 92.98 | 8233 |
| $CH_4$ conversion | 29.9% | 53.4% | 73.3% | 83.1% | 84.6% | 86.9% | 88.8% | 88.7% | 96.9% |
| $H_2$ (wt % of product) | 24.2% | 27.9% | 31.2% | 32.9% | 33.2% | 33.6% | 34.0% | 33.9% | 34.8% |
| Surplus $H_2$ (wt % of product) | 3.5% | 6.5% | 8.9% | 10.0% | 10.1% | 10.3% | 10.6% | 10.4% | 11.0% |

As shown in this table, the maximum acetylene yield increases rapidly with temperature until 1500° C. Above this temperature, the maximum acetylene yield increases at a slower rate. Further, the residence time required to achieve this conversion decreases with increasing temperature. For instance, at 1200° C., residence times over 1 second are needed, and acetylene comprises only about 8.6 wt % of the products, while at 1700° C., residence times of about 5 milliseconds are needed and acetylene comprises 44.0 wt % of the products. Residence time has a large impact on reactor volume (proportional to the reciprocal of residence time). As a result, a given unit of reactor may process more pyrolysis feed when the reactor temperature is high and residence time is low, which is shown in Table 1 as the $C_2H_2$/unit reactor volume. However, the very short residence times that achieve optimal acetylene yields at very high temperatures may place demands on certain reactor components that may exceed practicality. For example, where the pyrolysis feed is being flowed through the hot region of the pyrolysis reactor, the required gas velocity is roughly equal to the length of the hot region divided by the desired residence time. Gas velocities in flow channels and valve orifices are preferred to be less than the velocity of sound, which may result in reactor lengths that are not practical. In addition, because thermal pyrolysis involves the transfer of heat through a solid intermediary from a combustion step to a pyrolysis step, extremely short residence times may impose a heat transfer rate requirement (heat of reaction divided by reaction time) that may not be practical. As such, the design and operating conditions of the reactor may limit the maximum temperature that may be utilized to crack the given feed.

Even though maximum acetylene ($C_2H_2$) yield increases for methane with increasing temperature, the $C_{3+}$ yield is greatest for intermediate temperatures, such as 1400° C. Dividing $C_{3+}$ yield by acetylene yield gives a selectivity parameter ($C_{3+}/C_2H_2$) that indicates how much $C_{3+}$, which is related to coke production, has to be managed per unit of acetylene produced. This selectivity parameter remains very high (e.g., ≥0.5) for temperatures below 1500° C., and drops into a lower section (e.g., ≤0.45 or <0.4) for temperatures at or above 1500° C.

For feeds containing high levels of aromatics or methane, temperatures below 1500° C. are not as effective for production of acetylene because of the high $C_{3+}$ yields, the low acetylene yields, and the relatively long residence times (e.g., large reactor volumes) needed for processing. Conversely, considering the broad range of temperature cited for methane pyrolysis, there is an advantage to operating at temperatures above 1500° C., in terms of $C_2U$ yield and $C_2$ selectivity.

In addition, as shown in Table 1, pyrolysis of hydrogen-rich feed components of the pyrolysis feed, such as methane, result in substantial yield of hydrogen ($H_2$) gas. While the feed is composed of 20 wt % $H_2$ gas, the reactor product is composed on 24 wt % to 35 wt % $H_2$ gas. Surplus hydrogen may be calculated as the amount of $H_2$ remaining after conversion to some preferred product. In Table 1, surplus $H_2$ is calculated after subtracting the stoichiometric amount of $H_2$ utilized to convert the acetylene product to ethylene. For temperatures above about 1500° C., surplus $H_2$ remains roughly constant at about 10 wt % of the reactor product. Thus, the pyrolysis of hydrogen-rich hydrocarbon components of the pyrolysis feeds results in surplus $H_2$ that is available for use in the hydrotreating and pyrolysis of hydrogen-deficient feeds or for other processes.

The high severity pyrolysis is also substantially impacted by weight ratio of hydrogen ($H_2$) gas to feed hydrocarbon carbon (C), as shown in Table 2, below. Pyrolysis, in this example, is performed under isothermal conditions, for a feed containing methane gas and optionally hydrogen gas, at a temperature of 1550° C. and at 14.7 psig (101 kPag) reactor pressure. Residence time, in each case, is selected to give 70 wt % conversion of the methane feed. Table 2 lists the results, such as composition of the pyrolysis product (weight percent of total pyrolysis product) for operations at $H_2$/C levels between 0 and 5:

TABLE 2

| | $H_2/CH_4$ (molar ratio) | | | | | |
|---|---|---|---|---|---|---|
| | 0 | 1 | 2 | 3 | 4 | 5 |
| Residence time, sec | 0.004 | 0.007 | 0.011 | 0.014 | 0.018 | 0.021 |

TABLE 2-continued

| | $H_2/CH_4$ (molar ratio) | | | | | |
|---|---|---|---|---|---|---|
| | 0 | 1 | 2 | 3 | 4 | 5 |
| $CH_4$ Conversion: | 70.0% | 70.0% | 70.0% | 70.0% | 70.0% | 70.0% |
| $C_2U$, wt % | 28.2% | 34.7% | 36.0% | 35.1% | 33.4% | 31.6% |
| $C_{3+}$, wt % | 28.2% | 15.6% | 9.3% | 6.1% | 4.4% | 3.3% |
| Hydrogen ($H_2$), wt % | 13.5% | 23.1% | 30.7% | 37.0% | 42.2% | 46.7% |
| $C_{3+}/C_2U$ | 1.000 | 0.449 | 0.259 | 0.175 | 0.131 | 0.104 |
| relative $C_2$ productivity: | 509 | 280 | 168 | 111 | 78 | 57 |

As shown in Table 2, increasing hydrogen ($H_2$) diluent results has a small impact on $C_2U$ (e.g., acetylene and ethylene) yield, however increasing hydrogen diluent results in a substantial decrease $C_{3+}$ yield and corresponding decrease in $C_{3+}/C_2U$ weight ratio. Low hydrogen diluent levels may result in an unacceptably high level of $C_{3+}$ yield and corresponding decrease in $C_{3+}/C_2U$ weight ratio. High hydrogen diluent levels have a deleterious impact on reactor productivity because (a) the dilution reduces kinetic rates resulting in longer residence times (larger reactors) to achieve the same productivity, and (b) because $H_2$ dilution reduced the amount of hydrocarbon (and hence hydrocarbon products) that are carried in each volume of gas. These effects are reflected in the relative $C_2$ productivity entry in Table 2, which shows in relative terms the impact of hydrogen dilution on amount of $C_2$'s that are produced in a unit of reactor volume. High hydrogen dilution may also result in debits in process equipment outside of the pyrolysis reactor due to the larger volumes of gases that have to be managed per unit of pyrolysis product produced. Thus, there is an optimum amount of hydrogen diluent at moderate levels between 0 and 5. Accordingly, the present techniques, by means of high temperature pyrolysis, achieve at low $H_2/C$ molar ratio, a level of $C_{3+}/C_2U$ that would otherwise require operating at high (and less economical) levels of $H_2/C$.

Hydroprocessing feeds containing resid may result in significant conversion of the resid to lower molecular weight species, such as single and two ring aromatic compounds. Table 3 shows pyrolysis yields as an example of a lower molecular weight species resulting from hydrotreating. Typically these lower molecular weight compounds may be represented as hydrogen deficient feeds to the pyrolysis unit. As shown in Table 3 below, conditions and yields for the pyrolysis of hydrogen deficient feeds may be different than those for the pyrolysis of hydrogen rich feeds shown in Table 1. A hydrogen deficient feed, in this example toluene having 8.7 wt % hydrogen content, is pyrolysed at 1445° C., 4 psig (28 kPag) pressure, for a residence time of 0.08 seconds with a hydrogen diluent at a level of 28 moles $H_2$ gas per mole of hydrocarbon carbon. In this toluene conversion case, a high $H_2/C$ molar ratio is employed to compensate for a low pyrolysis temperature (1445° C.), while still achieving acceptable $C_{3+}/C_2U$ performance, thus illustrating features of toluene cracking. As indicated above, a more preferred operation would pyrolyze the toluene at higher temperature and lower $H_2/C$ molar ratio.

TABLE 3

| Pyrolysis of Toluene (8.7 wt % H) | | Products: wt % of toluene feed | | wt/wt ratio of products | |
|---|---|---|---|---|---|
| Pressure (psig) | 4 | Methane | 26% | $C_{3+}/C_2H_2$ | 0.351 |
| Temp (° C.) | 1445 | Ethylene | 12% | $C_{3+}/C_2U$ | 0.283 |

TABLE 3-continued

| Pyrolysis of Toluene (8.7 wt % H) | | Products: wt % of toluene feed | | wt/wt ratio of products | |
|---|---|---|---|---|---|
| Residence time (ms) | 80 | Acetylene | 49% | E/A | 0.238 |
| $H_2/C$ | 28 | $C_{3+}$ | 17% | | |
| | | $H_2$ | −5% | | |

As shown in Table 3, the pyrolysis results in a high conversion to acetylene (49 wt %) and ethylene (12 wt %), but also yields 17 wt % $C_{3+}$ materials (mostly coke and tar). In contrast to the pyrolysis of hydrogen rich feed (Table 1), the hydropyrolysis of hydrogen deficient feed results in a consumption of hydrogen (from the $H_2$ diluent), and the production of methane (26 wt % of feed toluene) as a product. Accordingly, it is advantageous to recycle the excess hydrogen ($H_2$) and methane gas that is produced from pyrolysis of hydrogen deficient feeds to be combined into the pyrolysis feed and/or to recycle the excess hydrogen ($H_2$) and methane gas that is produced from pyrolysis of hydrogen deficient feeds to be combined with the hydrocarbon feed in the hydroprocessing.

While the high-severity temperatures may be preferred if the objective of the process is to produce acetylene, variations in pressure along with the high-severity temperatures may enhance the distribution of $C_2$ compounds (e.g., yield of ethane, ethylene and acetylene) and the distribution of other light hydrocarbons (e.g., propylene, propyne, etc.). Accordingly, these pressure variations may be utilized if ethylene and/or other olefins are the preferred product. As an example, steam cracking typically utilizes lower temperature to convert ethane to ethylene and trace levels of acetylene. At atmospheric pressure, lower temperatures result in higher ethylene to acetylene (E/A) weight ratios. However, lower temperatures also provide poor conversions for methane and aromatics, which as noted above, is inefficient. At high-severity conditions (e.g., temperatures ≥1400° C. or preferably ≥1540° C., for example) aromatics and methane may be cracked at high conversion levels, with selectivity levels ≥50 wt % to light gas products. Also shown in Table 1, at temperatures ≥1400° C., selectivity levels ≥50 wt % to light gas products are achievable. For example, at 1540° C., products of methane make up 67.8 wt % of the pyrolysis product, including $H_2$, $C_2$'s, and $C_{3+}$. Thus, the selectivity to $C_{3+}$ is 20 wt % (13.7 wt %/67.8 wt %), and the selectivity to lighter gas products is 80 wt %. Further, by varying the pressure from atmospheric to elevated pressures (e.g., up to 300 psig (2068 kPag)), ethylene to acetylene (E/A) weight ratios ≥0.1, ≥0.2, ≥0.4 or even ≥0.5 may be achieved. The variations of pressure at high-severity operating conditions are described below in Tables 4 and 5 and FIGS. 1C to 1F.

Table 4 includes simulation results for different ratios of reactor products produced at different pressures for different temperatures from a methane feed. Pyrolysis, in this example, is carried out under isothermal conditions at 1500° C. and at 1650° C., with 2:1 molar diluent of hydrogen in a methane feed, and at 15 psig (103 kPag) reactor pressure to 162 psig (1117 kPag) reactor pressure. All products larger than $C_2$ are considered as $C_{3+}$ in this example and the product is the reaction product yield from the converted pyrolysis feed.

TABLE 4

| 70% Isothermal Conversion Data | | | | | | | | | Product ratios | | |
|---|---|---|---|---|---|---|---|---|---|---|---|
| Temp | P | time | | Products (weight percent) | | | | | | $C_{3+}/$ | |
| (° C.) | (psig) | (sec) | Conv. | $H_2$ | $CH_4$ | $C_2H_2$ | $C_2H_4$ | $C_{3+}$ | $C_2U$ | $C_2U$ | E/A |
| 1500 | 15 | 0.025 | 72% | 31.1 | 22.0 | 34.2 | 2.0 | 10.7 | 36.0 | 0.30 | 0.06 |
| 1500 | 36 | 0.025 | 73% | 31.1 | 21.7 | 32.7 | 3.1 | 11.3 | 36.0 | 0.32 | 0.10 |
| 1500 | 44 | 0.025 | 72% | 31.0 | 22.1 | 31.9 | 3.5 | 11.5 | 35.0 | 0.33 | 0.11 |
| 1500 | 59 | 0.025 | 71% | 30.7 | 23.3 | 30.3 | 4.1 | 11.6 | 34.0 | 0.34 | 0.14 |
| 1500 | 74 | 0.025 | 69% | 30.4 | 24.7 | 28.6 | 4.6 | 11.7 | 33.0 | 0.35 | 0.16 |
| 1500 | 103 | 0.025 | 65% | 29.7 | 27.9 | 25.4 | 5.4 | 11.5 | 31.0 | 0.37 | 0.21 |
| 1500 | 162 | 0.025 | 57% | 28.4 | 34.3 | 20.3 | 6.3 | 10.8 | 27.0 | 0.41 | 0.31 |
| 1650 | 15 | 0.0025 | 68% | 30.4 | 25.4 | 35.0 | 1.0 | 8.2 | 36.0 | 0.23 | 0.03 |
| 1650 | 36 | 0.0025 | 71% | 30.8 | 23.6 | 35.6 | 1.5 | 8.5 | 37.0 | 0.23 | 0.04 |
| 1650 | 44 | 0.0025 | 71% | 30.8 | 23.3 | 35.6 | 1.7 | 8.6 | 37.0 | 0.23 | 0.05 |
| 1650 | 59 | 0.0025 | 71% | 30.9 | 22.9 | 35.4 | 2.0 | 8.7 | 37.0 | 0.23 | 0.06 |
| 1650 | 74 | 0.0025 | 71% | 30.9 | 22.8 | 35.2 | 2.3 | 8.8 | 37.0 | 0.24 | 0.07 |
| 1650 | 103 | 0.0025 | 71% | 30.8 | 22.9 | 34.4 | 3.0 | 8.9 | 37.0 | 0.24 | 0.09 |
| 1650 | 162 | 0.0025 | 70% | 30.5 | 24.0 | 32.5 | 4.1 | 9.0 | 37.0 | 0.25 | 0.13 |

As shown in Table 4, as pressure increases from 15 psig (103 kPag) to 162 psig (1117 kPag), $C_2U$ yields in wt % of the product are roughly constant at about 33 wt % (+/−10 wt %) for 25 millisecond (ms) residence time at 1500° C. However, the E/A weight ratios improve over this increase in pressure. At 1650° C., the $C_2U$ yields in wt % of the product are again roughly constant at about 37 wt % (+/−10 wt %) for 2.5 ms, while the E/A weight ratio increases fourfold. Accordingly, the higher pressures tend to lead to higher E/A weight ratios. Further, the $C_{3+}$ yields in wt % of the product at these different temperatures and pressures also remain relatively constant at 12% for 1500° C. and 9% for 1650° C. As a result, the $C_{3+}$ to $C_2U$ weight ratio ($C_{3+}/C_2U$) increases at slow rate with pressure at the lower temperature, while the higher temperatures provide a roughly constant $C_{3+}$ to $C_2$ unsaturate weight ratio.

From this table, the yield of $C_2U$ (e.g., acetylene and ethylene) may be optimized for certain operating conditions. That is, a specific pressure, temperature and residence time may be utilized to optimize the distribution of $C_2U$ yield. These operating conditions may be characterized by the $C_{3+}$ to $C_2U$ weight ratio along with an E/A weight ratio, which may be further explained in view of the FIGS. 1C and 1D.

Figure 1C:
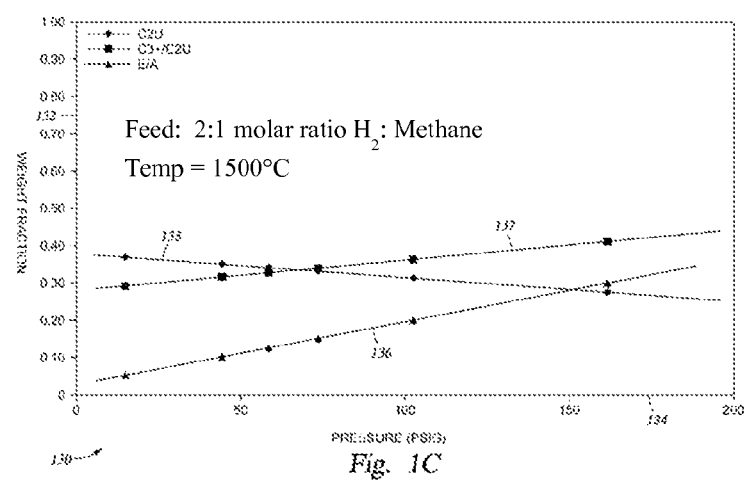
Figure 1D:
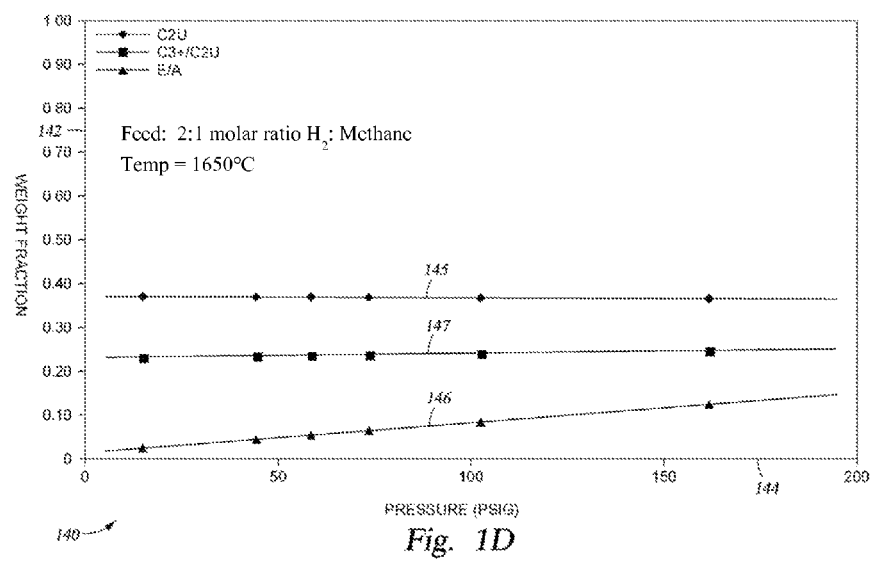

FIGS. 1C and 1D illustrate the simulation results for different ratios of reactor products produced at different pressures for certain temperatures from methane. The results of operating at the various pressures are provided for comparison of the product yields achievable at the residence times associated with the $C_2U$ yield and an E/A weight ratio for that pressure. Pyrolysis, in this example, is carried out under isothermal conditions, with 2:1 molar diluent of hydrogen in a methane feed, and at 1500° C. for diagram 130 and at 1650° C. for diagram 140. All products larger than $C_2$ are considered as $C_{3+}$ in this example and the product is the reaction product yield from the converted pyrolysis feed. In diagram 130, certain values for a $C_2U$ yield 135 in wt % of the product, ethylene to acetylene weight ratio 136, and $C_+$ to $C_2U$ weight ratio 137 are shown in weight fraction (or weight ratio) along the Y-axis 132 for various pressures (in psig) along the X-axis 134. The ethylene to acetylene weight ratio 136 and $C_{3+}$ to $C_2U$ weight ratio 137 increases with increasing pressure, while the $C_2U$ yield 135 decreases slightly with increasing pressure. Similarly, in diagram 140, certain values for a $C_2U$ yield 145 in wt % of the product, ethylene to acetylene weight ratio 146, and $C_{3+}$ to $C_2U$ weight ratio 147 are shown in weight fraction (or weight ratio) along the Y-axis 142 for various pressures (in psig) along the X-axis 144. The ethylene to acetylene weight ratio 146 increases with increasing pressure, while the $C_2U$ yield 145 and $C_{3+}$ to $C_2U$ weight ratio 147 are relatively constant with increasing pressure. As such, operating conditions of the thermal pyrolysis reactor may be adjusted to enhance the acetylene yield for a given feed.

Further, as it may be appreciated, different types of thermal pyrolysis reactors may have different heat profiles. That is, some embodiments of thermal pyrolysis reactors may operate in an isothermal manner with the heat profile being relatively constant, as noted above. However, other thermal pyrolysis reactors may have a heat profile that is similar to a Gaussian curve. For example, a regenerative reactor may be characterized by an initial and final temperature of 300° C. and a peak pyrolysis gas temperature of 1700° C. for a residence time of 35 ms (≤10 ms at temperature ≥1000° C.), the pressure effect on selectivity is even more dramatic as shown in Table 5 below.

The variations of pressure at high-severity operating conditions for a regenerative reactor are described below in Table 5 and FIGS. 1E and 1F. Table 5 includes simulation results for different weight ratios of reactor products produced at different pressures for different temperatures from a methane feed. Pyrolysis, in this example, is carried out under regenerative conditions resulting in a Gaussian-like temperature profile with inlet and outlet around 300° C. and with peak temperature of 1704° C. in one set of simulations and of 1783° C. in the other. About 25% of the residence time of the regenerative pyrolysis profile is at temperature above 1200° C. The pyrolysis of this example is carried out with 2:1 molar diluent of hydrogen in a methane feed, and at various reactor pressures between 4 psig (28 kPag) and 162 psig (1117 kPag). All products larger than $C_2$ are considered as $C_{3+}$ in this example and the product is the reaction product yield from the converted pyrolysis feed.

TABLE 5

| 70% Regenerative Conversion Data | | | | | | | | | Product ratios | | |
|---|---|---|---|---|---|---|---|---|---|---|---|
| Peak Temp | Pres. | time | | Products (weight percent) | | | | | | $C_{3+}/$ | |
| (° C.) | (psig) | (sec) | Conv. | $H_2$ | $CH_4$ | $C_2H_2$ | $C_2H_4$ | $C_{3+}$ | $C_2U$ | $C_2U$ | E/A |
| 1704 | 3 | 0.034 | 70% | 30.4 | 24.3 | 34.3 | 3.0 | 7.9 | 37.3 | 0.21 | 0.09 |
| 1704 | 15 | 0.034 | 72% | 30.7 | 22.2 | 33.6 | 5.0 | 8.4 | 38.6 | 0.22 | 0.15 |
| 1704 | 29 | 0.034 | 74% | 30.7 | 21.2 | 31.6 | 7.4 | 8.8 | 39.0 | 0.23 | 0.24 |
| 1704 | 36 | 0.034 | 74% | 30.6 | 21.0 | 30.5 | 8.5 | 8.9 | 39.0 | 0.23 | 0.28 |
| 1704 | 59 | 0.034 | 74% | 30.3 | 21.1 | 26.8 | 11.6 | 9.2 | 38.4 | 0.24 | 0.43 |
| 1704 | 103 | 0.034 | 71% | 29.4 | 23.1 | 20.1 | 15.6 | 9.1 | 35.7 | 0.26 | 0.78 |
| 1704 | 162 | 0.034 | 66% | 28.1 | 27.5 | 13.5 | 17.2 | 8.6 | 30.7 | 0.28 | 1.27 |
| 1783 | 15 | 0.011 | 67% | 30.0 | 26.5 | 33.4 | 3.0 | 7.1 | 36.3 | 0.20 | 0.09 |
| 1783 | 36 | 0.011 | 69% | 30.2 | 24.5 | 32.5 | 5.0 | 7.6 | 37.5 | 0.20 | 0.15 |
| 1783 | 44 | 0.011 | 70% | 30.2 | 24.2 | 31.9 | 5.8 | 7.8 | 37.6 | 0.21 | 0.18 |
| 1783 | 74 | 0.011 | 70% | 30.1 | 23.7 | 29.4 | 8.3 | 8.0 | 37.7 | 0.21 | 0.28 |
| 1783 | 103 | 0.011 | 70% | 29.8 | 23.8 | 26.7 | 10.6 | 8.1 | 37.3 | 0.22 | 0.40 |
| 1783 | 162 | 0.011 | 69% | 29.2 | 25.0 | 21.8 | 13.9 | 8.1 | 35.6 | 0.23 | 0.64 |

As shown in Table 5, as pressure increases from 3 psig (21 kPag) to 162 psig (1117 kPag), $C_2U$ yields decrease at a slow rate from 37 wt % to 31 wt % for a 33 ms residence time in a temperature profile that peaks at 1704° C. However, the E/A weight ratios increase rapidly with the increase in pressure. For the profile having peak temperature of 1784° C. and an 11 ms residence time, the $C_2U$ yields are roughly constant at about 37 wt %, while the E/A weight ratio again increases with increasing pressure. Accordingly, the higher pressures tend to lead to higher E/A weight ratios, while the $C_{3+}$ levels at these different temperatures and pressures remain relatively constant at around 8 wt % for the two profiles. As a result, the $C_{3+}$ to $C_2U$ weight ratio increases at slow rate for these different temperatures with the higher temperature providing roughly constant $C_{3+}$ to $C_2U$ weight ratio, but the E/A weight ratio increases at a larger rate. Moreover, higher pressures do not have a significant impact on $C_{3+}$ levels as the $C_{3+}$ to $C_2U$ weight ratio remains almost constant, which is an enhancement over the isothermal reactors.

From this table, the regenerative reactor may be utilized to further optimize the distribution the yield of $C_2U$ (e.g., acetylene yield relative to the ethylene yield) for certain operating conditions. That is, a specific pressure, temperature and residence time may be utilized to optimize the distribution of $C_2U$ yield along with the heat profile of the reactor. These operating conditions may be characterized by the $C_{3+}$ to $C_2U$ weight ratio along with an E/A weight ratio, which may be further explained in view of the FIGS. 1E and 1F.

Figure 1E:
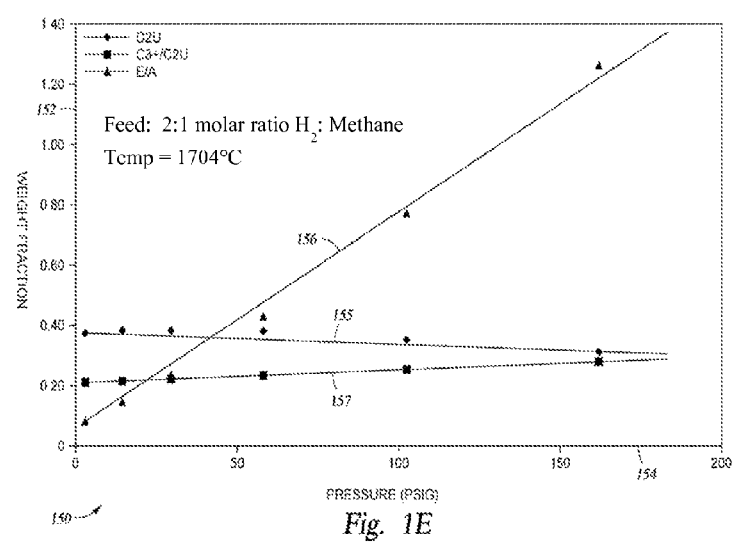
Figure 1F:
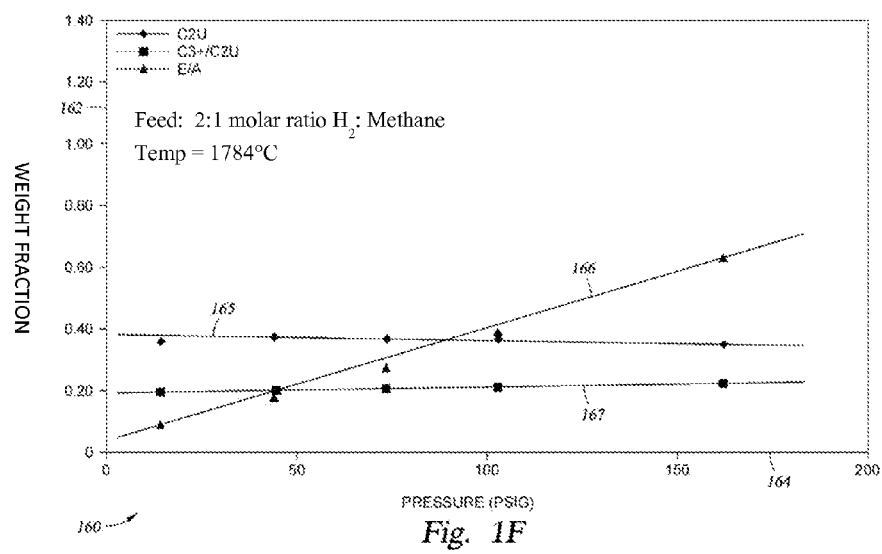

FIGS. 1E and 1F illustrate that the simulation results for different weight ratios of reactor products produced at different pressures for certain temperatures from a methane feed. The results of operating at the various pressures are provided for comparison of the product yields achievable at the residence times associated with the $C_2U$ yield and E/A weight ratio for that pressure. Pyrolysis, in this example, is carried out under regenerative reactor thermal conditions, with 2:1 molar diluent of hydrogen in a methane feed, and with a peak temperature of 1704° C. for diagram 150 and of 1784° C. for diagram 160. All products larger than $C_2$ are considered as $C_{3+}$ in this example and the product is the reaction product yield from the converted pyrolysis feed. In diagram 150, certain values for $C_2U$ yield 155 in wt % of the product, ethylene to acetylene weight ratio 156, and $C_{3+}$ to $C_2U$ weight ratio 157 are shown in weight fraction (or weight ratio) along the Y-axis 152 for various pressures (in psig) along the X-axis 154. The ethylene to acetylene weight ratio 156 and $C_{3+}$ to $C_2U$ weight ratio 157 increases with increasing pressure, while the $C_2U$ yield 155 decreases slightly with increasing pressure. Similarly, in diagram 160, certain values for $C_2U$ yield 165 in wt % of the product, ethylene to acetylene weight ratio 166, and $C_{3+}$ to $C_2U$ weight ratio 167 are shown in weight fraction (or weight ratio) along the Y-axis 162 for various pressures (in psig) along the X-axis 164. The ethylene to acetylene weight ratio 166 increases with increasing pressure, while the $C_2U$ yield 165 and $C_{3+}$ to $C_2U$ ratio 157 are relatively constant with increasing pressure. As such, operating conditions of the regenerative thermal pyrolysis reactor may be adjusted to enhance the distribution of the ethylene yield and/or acetylene yield for a given feed.

Although the E/A weight ratio continues to increase with increasing pressure, certain limiting factors may hinder higher pressure operations. For instance, eventually high pressure operating conditions may lead to unacceptable $C_{3+}$ to $C_2U$ weight ratios and/or lower $C_2U$ yields. Further, equipment utilized in the system may be limited to certain pressure ranges. Accordingly, preferred operating pressures may include pressures ≥4 psig (27 kPag), or ≥15 psig (103 kPag), or ≥36 psig (248 kPag), or ≥44 psig (303 kPag) or ≥103 psig (710 kPag), but may be ≤300 psig (2068 kPag), or ≤163 psig (1124 kPag), or ≤150 psig (1034 kPag). As may be appreciated, these different pressures may be combined together to form different combinations depending on the specific configuration of equipment.

In addition, it is beneficial to maintain longer residence times and lower temperatures to maximize E/A weight ratio. However, such residence times and temperatures result in higher weight ratios of $C_{3+}$ to $C_2U$. Accordingly, the design and operating conditions may be adjusted to provide a balance between the E/A weight ratio and the $C_{3+}$ to $C_2U$ weight ratio. That is, the thermal pyrolysis reactor may be operated at lower temperatures to maximize the E/A weight ratio at an efficient and operable $C_{3+}$ to $C_2U$ weight ratio. Alternatively, when lower weight ratios of E/A are preferred, the reactor may be operated at higher temperature and at lower pressure to minimize the E/A weight ratio at an efficient and operable $C_{3+}$ to $C_2U$ weight ratio. As an example, the operating conditions, such as the peak pyrolysis gas temperatures and/or pressure, of the thermal pyrolysis reactor may be adjusted based on an optimized value from an optimization function that comprises an ethylene to acetylene weight ratio and the $C_{3+}$ to $C_2$ unsaturate weight ratio.

The thermal pyrolysis reactor may be limited to certain pressures by various limitations. For instance, at higher pressures and constant residence times, mass density of the gas increases and thus requires higher heat transfer rates per unit of reactor volumes. This heat transfer rate may exceed the capability of the reactor internals or may lead to exceedingly small channels or exceedingly large numbers of channels per square inch (CPSI). Thus, these limitations may eventually lead to impractical reactor dimensions and impractically high levels of pressure drop.

Unless otherwise stated, all percentages, parts, ratios, etc., are by weight. Unless otherwise stated, a reference to a compound or component includes the compound or component by itself, as well as in combination with other compounds or components, such as mixtures of compounds. Unless otherwise stated, all pressures are given as gauge that is as pressure above ambient atmospheric pressure (e.g., psig).

Further, when an amount, concentration, or other value or parameter is given as a list of upper preferable values and lower preferable values, this is to be understood as specifically disclosing all ranges formed from any pair of an upper preferred value and a lower preferred value, regardless whether ranges are separately disclosed.

The terms "convert" and "converting" are defined broadly herein to include any molecular decomposition, cracking, breaking apart, conversion, and/or reformation of organic molecules (hydrocarbons) in the feed, by means of at least pyrolysis heat, and may optionally include supplementation by one or more of catalysis, hydrogenation, diluents, and/or stripping agents.

As used herein, the expression "non-volatiles" may be defined broadly herein to mean substantially any resid, metal, mineral, ash, ash-forming, asphaltenic, tar, coke, and/or other component or contaminant within the feedstock that does not vaporize below a selected boiling point or temperature and which, during or after pyrolysis, may leave an undesirable residue or ash within the reactor system, which is difficult to remove. More specifically, the term "resid", as used herein, refers to a non volatile fraction of the feed, having a normal boiling point above about 565° C. (e.g., fraction heavier than 565° C. or 565+° C.). Resid conversion is defined as the conversion of a bottoms fraction or 565+° C. fraction of a feed to a lighter 565−° C. fraction (e.g., fraction lighter than 565° C.) via thermal, hydrothermal or catalytic liquid cracking. Distillation fractions of a feed can be determined using test methods ASTM D2887 or D1160. The terms 'heavy' and 'light' in reference to a hydrocarbon fraction refers to the hydrocarbon's boiling point, with 'heavy' referring to fractions having higher boiling point (i.e. boiling at higher temperature) and 'light' referring to fractions having lower boiling point. Boiling points, when used to characterize fractions (e.g., fraction heavier than 565° C.) are given at atmospheric pressure, although actual distillation may be carried out at reduced temperature and pressure, as is known in the art. Non-combustible non-volatiles may include ash, for example. Methods for determining asphaltenes and/or ash may include American Society of Testing and Materials (ASTM) methods, such as methods for asphaltenes may include ASTM D-6560 and D-7061 and methods for ash may include ASTM D-189, D-482, D-524, and D-2415. In the context of a pyrolysis feed, non-volatiles are materials that are not in the gas phase (i.e. are components that are in the liquid or solid phase) at the temperature, pressure and composition conditions of the inlet to the pyrolysis reactor. Non-combustible non-volatiles (e.g., ash; ASTM D-189) in the pyrolysis feed are preferably limited to ≤2 parts per million weight (ppmw) on pyrolysis feed, more preferably ≤1 ppmw. Combustible non-volatiles (e.g., tar, asphaltenes, ASTM D-6560) may be present in the pyrolysis feed at concentrations below 5% of the hydrocarbons in the pyrolysis feed, preferably at concentrations below 1%, more preferably at concentrations below 100 ppmw, and most preferably at concentrations below 10 ppmw of the total hydrocarbons of the pyrolysis feed to the pyrolysis reactor, as long as the presence of the combustible non-volatiles do not result in excessive (e.g., ≥2 or ≥1 ppmw) concentrations of non-combustible non-volatiles. Hydrocarbon feeds may also be characterized, for example using Nuclear Magnetic Resonance (NMR), for aromatic carbon content, which is a measure of the hydrocarbon that is within aromatic ring structures. The "aromatic carbon content", as used herein, is the weight percent on feed of carbon contained in an aromatic ring. Aromatic carbon conversion is defined as the percent of a hydrocarbon's aromatic carbon that is saturated to non-aromatic material during a hydro-conversion process. For example, the hydro-conversion of naphthalene (10 aromatic carbons) to tetralin (4 aliphatic and 6 aromatic carbons) results in a 40% aromatics conversion.

As used herein, the terms "coke" and "soot" may refer to hydrocarbonaceous material that accumulates within the reactor during pyrolysis or to solid-phase hydrocarbonaceous materials that emerge from the reactor with pyrolysis effluent. The hydrocarbonaceous material that accumulates within the reactor during pyrolysis may also be defined as the fraction of the pyrolysis feed that remains in a thermal pyrolysis reactor and thus does not emerge from the reactor as pyrolysis effluent. Coke and soot are components of the reactor product, which are included for $C_{3+}$ product for pyrolysis selectivity. The terms "$C_3^+$" and "$C_{3+}$" mean all products of the pyrolysis feed having more than three carbon atoms, which include coke and soot, whether those products emerge from the reactor or remain within the reactor. The reactor product that does emerge may be referred to as the reactor effluent, which is at least a portion of the reactor product.

The term "pyrolysis feed" means the composition, which may be a mixture, subjected to pyrolysis. In one embodiment, the pyrolysis feed is derived from a hydrocarbon feed (e.g., by separation of a portion from the hydrocarbon feed and optional addition of diluents).

As used herein, the "hydrocarbon feed" contains hydrocarbons (C bound to H) and may contain (i) minor components of heteroatoms (≤10 wt %) covalently bound to hydrocarbons and (ii) minor components of heteroatoms (≤10 wt %) not bound to hydrocarbons (e.g., $H_2O$), wherein these weight percents are based on the weight of the hydrocarbon feed. The term "hydrocarbons in the hydrocarbon feed" or "hydrocarbons of the hydrocarbon feed" means molecules within the hydrocarbon feed that contain at least hydrogen and carbon and, optionally, heteroatoms covalently bound to a portion of such molecules. Weight percents of hydrogen and carbon, as used to characterize the hydrocarbon feed, are provided as a percent of the hydrocarbons in the hydrocarbon feed. The hydrocarbon feed may include, by way of non-limiting examples, one or more of Fischer-Tropsch gases, methane, methane containing streams such as coal bed methane, biogas, associated gas, natural gas and mixtures or components thereof, steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, hydrocarbon streams derived from plant or animal matter, and/or any mixtures thereof.

As used herein, the expression "advantaged feed" means a feed that has a lower cost (per ton or per heating value) than Brent reference crude oil and may include, by way of non-limiting examples, one or more methane containing feeds and one or more high-aromatic containing streams. Some examples may include one or more of Fischer-Tropsch gases, methane, methane containing streams such as coal bed methane, biogas, associated gas, natural gas and mixtures or components thereof, steam cracked gas oil and residues, gas oils, coker naphtha, steam cracked naphtha, catalytically cracked naphtha, hydrocrackate, reformate, raffinate reformate, natural gasoline, Fischer-Tropsch liquids, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, and/or any mixtures thereof.

The term "hydrogen content" means atomic hydrogen bound to carbon and/or heteroatoms covalently bound thereto and which excludes molecular hydrogen ($H_2$) in the hydrocarbon feed expressed as a weight percent based on the weight of the hydrocarbons in the hydrocarbon feed. Hydrogen content as applied to pyrolysis feed or reactor feed are expressed as an ASTM weight percent of hydrocarbons in the respective feed. As used herein, the expression "low hydrogen content feed" or "low hydrogen content hydrocarbon feed" means a feed with a hydrogen content of ≤about 13 wt %. The hydrogen content of hydrocarbon feeds, reactants and products for present purposes can be measured using any suitable protocol, e.g., ASTM D4808-01(2006) Standard Test Methods for Hydrogen Content of Light Distillates, Middle Distillates, Gas Oils, and Residua by Low-Resolution Nuclear Magnetic Resonance Spectroscopy or ASTM D5291-10 Standard Test Methods for Instrumental Determination of Carbon, Hydrogen, and Nitrogen in Petroleum Products and Lubricants. Examples of the low hydrogen content hydrocarbon feeds include one or more of steam cracked gas oil and residues, gas oils, heating oil, diesel, gasoline, coker naphtha, steam cracked naphtha, catalytically cracked naphtha, reformate, raffinate reformate, distillate, crude oil, atmospheric pipestill bottoms, vacuum pipestill streams including bottoms, heavy non-virgin hydrocarbon streams from refineries, vacuum gas oil, heavy gas oil, atmospheric resid, heavy residuum and mixtures thereof. The low hydrogen content hydrocarbon feedstock may have a nominal end boiling point of at least 400° F. (204° C.), (e.g., ≥400° F., such as in excess of 1200° F. and even in excess of 1500° F.) and commonly has a nominal end boiling point of at least 500° F. (260° C.). Some preferred hydrocarbon feedstocks include crude oil, atmospheric and vacuum resids, tars, fuel oils and cycle oils. Such heavier, more aromatic feeds are typically lower cost, per unit weight, but may yield lower acetylene and ethylene yields and higher carbon or tar yields. Especially preferred feeds include aromatic feed, gas oils, cracked gas oils, crude, atmospheric resid feed, vacuum resid feed, tars, and heavy feed containing pitch. Due to the high aromatic content of the heavier feeds, the feeds have low hydrogen content (typically ≤13 wt % or even ≤11 wt % atomic hydrogen content). During pyrolysis, the hydrogen deficient feeds may form tar, coke, or soot.

The hydrocarbon feed along with a hydrogen containing stream are provided to a hydrotreating unit to form a hydrotreated product, which may be optionally provided directly to reactor without intervening processing. The hydrocarbon feed may optionally be mixed with a diluent hydrocarbon feed prior to the hydroprocessing (e.g., hydrotreating, hydrocracking or hydrogen donor processing) or in the hydrotreating unit in certain embodiments. The hydroprocessed (e.g., hydrotreated product) may have a portion of it removed to form the pyrolysis feed and/or may be combined with a hydrogen ($H_2$) containing stream to form the pyrolysis feed. That is, the pyrolysis feed may be derived from the hydrocarbon feed and/or hydroprocessed product. The pyrolysis feed may include hydrogen gas ($H_2$) in an amount that provides a preferred molar ratio of hydrogen (H) to carbon (C) considering the hydrocarbon components and hydrogen ($H_2$) gas in the combined pyrolysis feed. The atomic hydrogen to carbon (H/C) ratio of the combined hydrogen ($H_2$) and hydrocarbon of the pyrolysis feed may be from 3 to 15, such as 3, 5, 6, 7, 8, 10, 15, or values in between. Carbon in non-hydrocarbon species (e.g., $CO_2$) should be excluded for the purpose of this H/C calculation, as should hydrogen bound to oxygen (e.g., in $H_2O$). For some embodiments, the pyrolysis feed may have a hydrogen gas ($H_2$) to feed carbon molar ratio is 0 or 0.1 to 5, which may be adjusted by the addition of hydrogen ($H_2$) to form the pyrolysis feed. Combining the hydrogen content of the hydrogen gas to the hydrogen and carbon contents of the hydrocarbon components of the pyrolysis feed may result in a weight percent of total hydrogen in the pyrolysis feed that is greater than that in the hydrocarbon feed. For example, the weight percent of total hydrogen in the pyrolysis feed may be between 8 wt % and 54 wt %.

As used herein, the expression "combustion feed" means the two or more individual feeds that are to be combined to form a combustion reaction or a mixture of two or more feeds, such as a combustion fuel that does not contain oxidants (e.g., $O_2$) or non-combustible non-volatiles and a combustion oxidant that may include an oxygen or oxygen containing fluid. The combustion fuel may include, by way of non-limiting examples, one or more of Fischer-Tropsch gases, methane, methane containing streams such as coal bed methane, biogas, associated gas, natural gas and mixtures or components thereof, synthesis gas (mixtures of CO and $H_2$) and hydrogen. The combustion oxidant may include, but are not limited to, air, oxygen or mixtures thereof. Any of the combustion feed, fuel, or oxidant may additionally include non-combustible but volatile diluents such as $N_2$, $CO_2$, $H_2O$, and/or other inert gases.

The term "reactor", as used herein, refers to equipment used for chemical conversion. As such, several items identified as reactors may be combined to become a single entity that is also identified as a reactor, in that individual and combined entities may all be characterized as equipment used for chemical conversion. The regenerative reverse-flow thermal pyrolysis reactors described herein may comprise first and second reactor entities, for example as described in U.S. Patent App. Pub. No. 2007/0191664.

The term "pyrolysis reactor", as used herein, refers to a system for converting hydrocarbons by means of at least pyrolysis chemistry. The pyrolysis reactor may include one or more reactors and/or associated equipment and lines. A region, as used herein, refers to a location within the pyrolysis reactor, which may include one or more reactors and/or associated equipment and lines. The region may include a specific volume within a reactor, a specific volume between two reactors and/or the combination of different disjointed volumes in one or more reactors. The regenerative reverse-flow thermal pyrolysis reactors described herein may comprise first pyrolysis reactor and second pyrolysis reactor, for example as described in U.S. Patent App. Pub. No. 2007/0191664.

As used herein, the "thermal pyrolysis reactor" includes at least predominantly pyrolysis chemistry. Pyrolysis or pyrolysis chemistry, such as the conversion of hydrocarbons to unsaturates such as ethylene and acetylene, is an endothermic process requiring addition of heat. The terms crack and cracking may be used interchangeably with the terms pyrolyse and pyrolysis. In a thermal pyrolysis reaction, ≥50%, ≥80%, or ≥90%, of this heat is provided by heat transfer via solid surfaces such as tubulars or bed materials. Any combustion chemistry that occurs within the pyrolysis stream of a thermal pyrolysis reactor provides a minority of the endothermic heat of pyrolysis, such as ≤50%, ≤20%, or ≤10% of the endothermic heat of pyrolysis.

Other examples include U.S. patent Ser. No. 12/119,762 and Ser. No. 12/121,353, which are each incorporated by reference, describe a process and regenerative pyrolysis reactor utilized for pyrolyzing a hydrocarbon feedstock containing resid. Finally, U.S. Patent Ser. No. 61/349,464, which is incorporated by reference, describes a process and regenerative pyrolysis reactor utilized for pyrolyzing a hydrocarbon feedstock.

The term "high-severity operating conditions" means pyrolysis conditions resulting in the conversion of the a pyrolysis feed comprising hydrocarbons to make a product having an acetylene content ≥10.0 wt % based on the weight of the hydrocarbons in the pyrolysis feed. The operating conditions for a thermal pyrolysis reactor may be characterized by a severity threshold temperature that divides low-severity operating conditions in thermal pyrolysis reactors from high-severity operating conditions in thermal pyrolysis reactors. The severity threshold temperature is defined as the lowest temperature at which the feed to the reactor may react at a residence time ≤0.1 sec (second) to make at least 10 wt % acetylene as a percent of the hydrocarbons in the feed evaluated at the given operating conditions of the process. The high-severity operating conditions for a thermal pyrolysis reactor may be characterized as peak pyrolysis gas temperatures that are greater than the severity threshold temperature. The low-severity thermal pyrolysis reactor may be characterized as pyrolysis gas temperatures that are less than the severity threshold temperature and no pyrolysis gas temperatures that exceed the severity threshold temperature. For example, for the thermal conversion of methane at a pressure of 14.7 psig (101 kPag) and with 2:1 molar ratio of hydrogen diluent, the threshold temperature is about 1274° C. for this process. At temperatures at or above 1274° C., yields of acetylene can exceed 10 wt % of the starting methane, at some time ≤0.1 seconds. Conversely, at temperatures below 1274° C., there are no times ≤0.1 seconds for which yields of acetylene reaches 10 wt % of the starting methane. A similarly-defined severity threshold temperature may be used to distinguish between high-severity and low-severity types of other reactors, such as partial combustion, indirect combustion, and arc processes. That is, if that reactor operation is capable of converting the hydrocarbon feed to ≥10% acetylene at a residence time of ≤0.1 seconds, that reactor is considered a high-severity reactor.

According to one or more embodiments of the present techniques, an enhanced process is provided for the production of $C_2U$ (e.g., acetylene and ethylene), which are useful for manufacturing polyolefins and other petrochemical products. The process may include various stages, such as feed preparation that involves hydrotreating, pyrolysis, recovery and further processing, such as separation of the polymer grade monomer and polymerization to polyethylene. The thermal pyrolysis reactor may have operating conditions that are below a specific selectivity threshold, such as a $C_{3+}$ to acetylene weight ratio ≤0.5, or <0.45 or ≤0.4. Operation at low levels of $C_{3+}$ to acetylene is desirable both to improve process economics and to improve process operability. Economics are improved by low $C_{3+}$ to acetylene weight ratio because $C_{3+}$ products produced by high-severity pyrolysis are less valuable than the acetylene product. Further, operability is enhanced by low $C_{3+}$/acetylene weight ratio because $C_{3+}$ products may include substantial amounts of coke, whose production may hinder operations. Specifically, coke produced in excess amounts may result in an inability to maintain the thermal pyrolysis reactor channels available for fluid flow, and coke produced in excess amounts may result in heat release (during combustion and/or regeneration steps), which is greater than the heat amounts that may be used in the process or reactor. The reactor product from the reactor may be further processed to recover polyethylene, polyolefins, benzene or other products.

Further, in one or more embodiments of the present techniques, an enhanced process is provided for the production of a specific distribution of $C_2U$ (e.g., acetylene yield and ethylene yield), which are useful for manufacturing polyolefins and other petrochemical products. In particular, the present techniques may involve operating conditions that may include a $C_{3+}$ to $C_2U$ weight ratio ≤0.5, ≤0.4, or ≤0.3, while the ethylene to acetylene weight ratio is ≥0.02, or ≥0.1, or ≥0.2 or ≥0.5. These operating conditions may be utilized to manage the amount of ethylene and acetylene for further processing. By managing the size and capacity of the equipment for acetylene conversion, the process units may be smaller and involve less capital expense. Further, by operating at certain pressure ranges, the use of compression for recovery stages may be minimized or eliminated.

Accordingly, the present techniques may involve operating the thermal pyrolysis reactor at different operating conditions to perform the hydropyrolysis. These operating conditions may include adjusting operational settings to adjust the pressure within the reactor and/or the temperature within a reactor. The operational settings may include increasing the heat generated by providing different combustion feeds to the thermal pyrolysis reactor. The present techniques may be further understood with reference to the FIGS. 2 to 4, which are discussed below.

The present techniques utilize hydrotreating to enhance the process of the high-severity pyrolysis. The process utilizes the hydrogen produced from the cracking of the feed in the reactor as a recycle product (e.g., hydrogen ($H_2$) containing stream). As part of this process, the high-severity operating conditions involve higher temperatures, which produce more hydrogen ($H_2$) than other processes at low-severity operating conditions without producing larger amounts of coke. Unlike other processes, such as visbreaking, this process utilizes enough hydrogen (H2) to do mild feed hydrotreating to catalytically convert at least a portion of the hydrocarbons in the feed into a vapor product that may be converted in the thermal pyrolysis process into $C_2U$. This is an enhancement over other processes, such as visbreaking, which produces less vapor product without fouling. Further, the integration of hydrotreating and high-severity pyrolysis does less sulfur conversion compared to other processes. That is, the hydrotreating does less heteroatom species conversion (e.g., conversion of mercaptan and benzyl thiophenes), which are managed in the thermal pyrolysis step and/or downstream of the thermal pyrolysis step.

Figure 2:
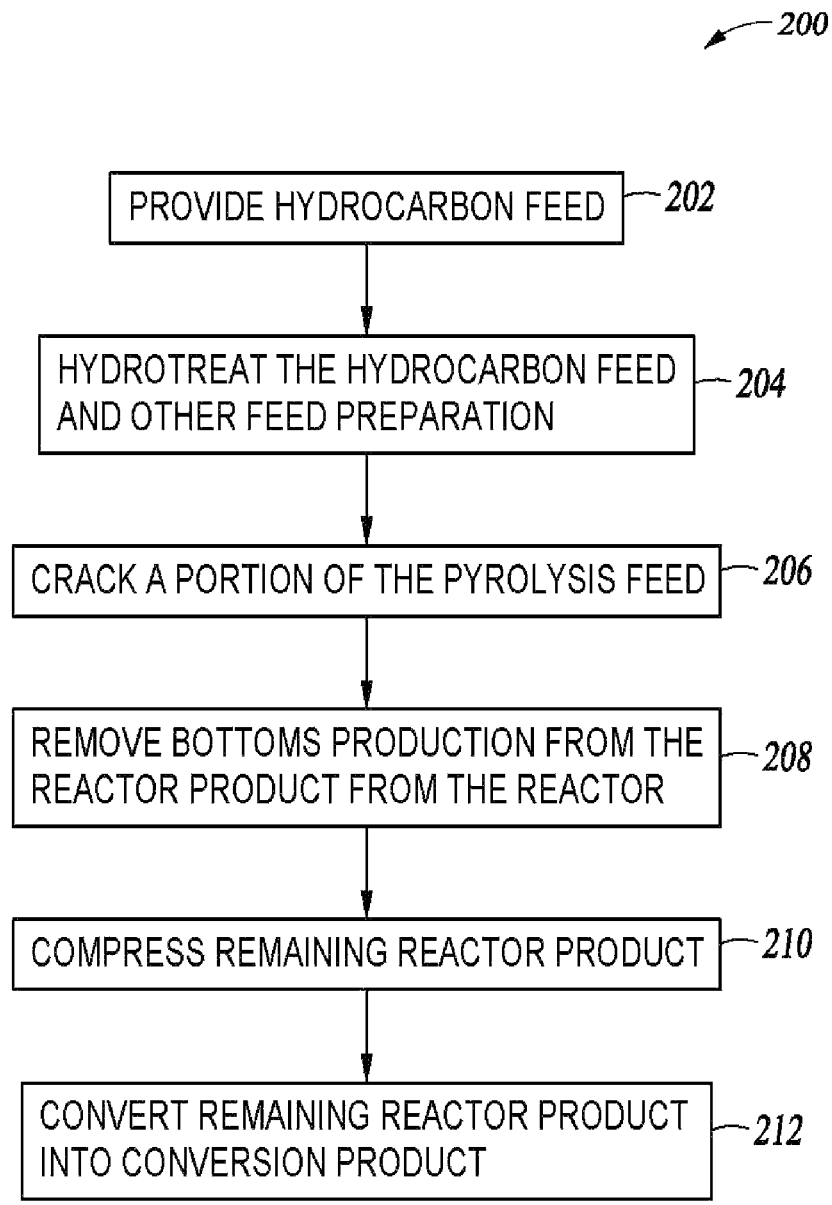
FIG. 2 is a simplified process flow diagram illustrating an embodiment of the present techniques.

To begin, an exemplary embodiment of the present techniques is illustrated in the block flow diagram 200 of FIG. 2. In this flow diagram 200, a process for the production of conversion products, such as ethylene, is shown, which subsequently may be used in the manufacture of polyolefins, such as polyethylene. In this block diagram, the process includes various stages. For instance, a feed preparation stage that involves hydrotreating is described in block 204. A cracking stage is described in block 206, which involves cracking the pyrolysis feed in a thermal pyrolysis reactor, which produces a reactor product. The pyrolysis reactor may be utilized at high-severity operating conditions that manage the $C_{3+}$ to $C_2U$ weight ratio ≤0.5, or ≤0.4, or ≤0.3, while the ethylene to acetylene weight ratio is ≥0.02, or ≥0.1, or ≥0.2 or ≥0.5. Further, the reactor may be operated at operating conditions that produce a reactor product that has $C_{3+}$/acetylene weight ratio of ≤0.5, or ≤0.45, or ≤0.4. The $C_2U$ components (e.g., acetylene and ethylene) of the reactor product may represent ≥20 wt %, or ≥50 wt %, or ≥80 wt %, or ≥90 wt % of the total $C_2^+$ gas phase components of the reactor product. Then, a recovery stage is described in blocks 208 to 212, which further processes at least a portion of the reactor product or reactor effluent to recover ethylene, propylene, and/or other polyolefins.

At block 202, a hydrocarbon feed, which may have a resid content of ≥10 wt % and poor volatility, is provided. As noted above, the hydrocarbon low hydrogen content hydrocarbon feed may contain ≤about 13 wt % atomic hydrogen, ≤about 11 wt % atomic hydrogen, or ≤about 8 wt % atomic hydrogen. The feed may contain non-volatiles or have a fraction with boiling point greater than 565+° C. The feed may have ≥10 wt %, ≥20 wt % or even ≥30 wt % resid that boils above 565° C. The feed may or may not have aromatic carbon. For instance, the feed may have an aromatic carbon content ≥1 wt %, ≥20 wt % or even ≥70 wt %. Examples of the hydrocarbon feed may include one or more of cracked gas oil, tars and residues, atmospheric pipestill bottoms, vacuum pipestill streams, for example. As an example, the hydrocarbon feed may contain ≥1 wt % aromatic carbon content and ≤20 wt % of the aromatic carbon in the hydrocarbon feed may be converted in the hydrotreating unit to non-aromatic carbon.

At block 204, the hydrocarbon feed may be subjected to various feed preparation processes prior to cracking a portion of the feed. For example, the feed preparation processes include one and optionally more hydroprocessing stages. The hydroprocessing processes may include thermal or catalytic hydrotreating or hydrocracking, one or more of hydrovisbreakers, hydrocrackers, high conversion (thermal) hydrotreaters, catalytic hydrogenation units or resid hydroprocessing units or residfiners. These hydrotreaters are described in *Kirk-Othmer Encyclopedia of Chemical Technology*, 4th edition, Volume 9, John Wiley & Sons, 1996. A preferred hydrotreating unit may be a hydroprocessing unit, such as a hydrovisbreaker, resid hydrocracker or resid hydrotreater that yields significant 565° C. boiling point conversion or non-volatile conversion. The hydrotreating unit may operate at low hydrogen partial pressure to avoid hydrogen incorporation or aromatic saturation. The hydrotreating unit may operate at pressures between 200 psig and 2000 psig (between 1379 kPag and 13789 kPag) and at space velocities (LHSV) from 0.1 to ≥20. The hydrotreating may be performed at reaction temperatures between 350° C. and 500° C. Hydrogen consumption for the hydrotreating process may be as low as 200 standard cubic feet per barrel (scf/bbl) and as high as 2000 scf/bbl at higher hydrogen pressures. The hydrotreating processes may involve combining the hydrocarbon feed containing resid with a hydrogen containing stream, which may be a separate stream or a recycle product (e.g., hydrogen product) from the recovery stage. Preferably, the hydroprocessing converts the non-volatile components to lighter volatile hydrocarbons. Resid conversion may be ≥20 wt %, ≥40 wt %, ≥50 wt %, ≥60 wt % or ≥80 wt %. The hydrotreating process may also convert aromatic carbon to aliphatic carbon. Preferably, aromatic carbon conversion is less than the amount of the non-volatile conversion. Hydrotreating or hydrovisbreaking, which each include a catalyst for enhanced conversion, is preferred over visbreaking because hydrotreating increases resid conversion and reduces downgrading heavier components. Aromatic carbon conversion may be ≤10 wt %, ≤20 wt %, ≤30 wt % or ≤50 wt %. In some embodiments of the present invention, the extent of aromatic carbon conversion may be less than half of the extent of resid conversion, less than one-fourth of the extent of resid conversion or less than one-sixteenth of the extent of resid conversion.

Further, the feed preparation may optionally include removal of impurities or contaminants or removals of metal impurities or resid or other non-volatiles after hydrotreating and prior to cracking. The feed preparation process may also include mixing the hydrocarbon feed with a diluent, such as hydrogen or another hydrocarbon feed. The feed preparation processes may include one or more of condensate and water removal units, acid gas removal units (e.g., caustic or amine treater units), dehydration units (e.g., glycol units), nitrogen removal units, demetalation, visbreaking, coking and/or vapor/liquid separators. The impurities or contaminants, which may include one or more of carbon dioxide, carbon monoxide, sulfur species, oxygenates and non-volatiles (e.g., metal), may be conducted away from the process.

After the feed preparation stage, the pyrolysis feed is cracked in block 206. The pyrolysis feed may be a portion of the hydroprocessed product (e.g., hydrotreated product) or may be a portion of the hydroprocessed product combined with a hydrogen containing stream. The cracking of the pyrolysis feed may involve the use of a thermal pyrolysis reactor to convert the pyrolysis feed into a reactor product (e.g., reactor effluent). The reactor product includes one or more $C_2U$, and optionally includes hydrogen ($H_2$), methane, ethane, methyl acetylene, diacetylene, and $C_{3+}$ products (e.g., benzene, coke, tars, soot, etc.). The reactor product includes components that emerge from the reactor and those that remain within the reactor, if any, as a result of pyrolysis (e.g., coke may remain in the reactor and later emerge as a portion of the combustion products). The amount of coke remaining in the reactor may be determined from a mass balance of the process. Further, in block 206, the thermal pyrolysis reactor may include any of a variety of thermal pyrolysis reactors, such as a regenerative reverse flow reactor, as described in U.S. Patent App. Pub. No. 2007/0191664. Other embodiments may include a thermal pyrolysis reactor, as described in U.S. Pat. No. 7,491,250, U.S. Patent Ser. No. 61/349,464 and U.S. Patent App. Pub. Nos.

2007/0144940 and 2008/0142409. Regardless of the specific type of thermal pyrolysis reactor, it may operate at peak pyrolysis gas temperatures between 1200.0° C. and 2200.0° C., preferably between 1400.0° C. and 1900.0° C. In particular, for reactors with an isothermal heat profile, the temperatures may be between 1450.0° C. and 1700.0° C., or between 1540° C. and 1650° C. For reactors with a Gaussian like heat profile, the peak pyrolysis gas temperatures may be in the range of 1540.0° C. to 2200.0° C. or 1600.0° C. to 1800.0° C. Further, the preferred operating pressures may include pressures ≥4 psig (28 kPag), or ≥15 psig (103 kPag), or ≥36 psig (248 kPag), or ≥44 psig (303 kPag) or ≥103 psig (710 kPag), but may be ≤300 psig (2068 kPag), or ≤163 psig (1124 kPag), or ≤150 psig (1034 kPag). As may be appreciated, these different pressures and temperatures may be combined together to form different combinations depending on the specific configuration of equipment. Further, for a regenerative reverse flow reactor, the pressure in the pyrolysis step may be similar or different to the pressure in the combustion step (e.g., at lower or higher pressure than the pyrolysis step).

At least a portion of the reactor product may be conducted away for storage or further processing. Optionally, one or more upgrading processes may be included in the recovery stage, as shown in blocks 208 to 212. At block 208, the at least a portion of the reactor product may be subject to a separation process to provide a bottoms product. The separation may remove one or more bottom products comprising solids, such as higher boiling point materials (e.g., contaminates, solids or impurities) from the $C_2U$ in reactor product. The separation process may include a tar and/or solid removal process, compression, adsorption, distillation, washing, and drying of the remaining reactor product, and/or any combination of one or more of these processes.

At block 210, the remaining reactor product may be optionally compressed. The compression may include compressors that operate at outlet pressures pressure from 50 psig (345 kPag) to 400 psig (2758 kPag), or more preferably from 150 psig (1034 kPag) to 300 psig (2068 kPag).

At block 212, the remaining reactor product may optionally be provided to a conversion process, such as acetylene conversion. The remaining reactor product may be in liquid phase, vapor phase or a mixture thereof, and may be subjected to a conversion process that is performed by a catalyst in the liquid phase, vapor phase or a mixture thereof. For instance, the conversion process may be an acetylene conversion process, which includes acetylene hydrogenation in an isothermal, slurry or adiabatic catalytic reactor, or other suitable conventional techniques. The catalytic reactor may employ group VI or VIII catalyst, catalyst bimetal or trimetal blends on an alumina, silica or other support, as is well known in the art. For example, the acetylene in the reactor product is absorbed into a liquid, hydrogenated within that liquid and then the ethylene product is desorbed from the liquid. The conversion products, which include ethylene, may optionally be provided to a purification process. The purification process may include (multistage) distillation or refrigerated distillation including a demethanator tower and $C_2$ splitter.

Should additional upgrading or purification of the conversion products be desired, purification systems, such as that found in *Kirk-Othmer Encyclopedia of Chemical Technology*, 4th edition, Volume 9, John Wiley & Sons, 1996, pg. 894-899, may be used. In addition, purification systems, such as that described in *Kirk-Othmer Encyclopedia of Chemical Technology*, 4th edition, Volume 20, John Wiley & Sons, 1996, pg. 249-271, may also be used. Other examples may be found in U.S. Pat. Nos. 6,121,503; 5,960,643; 5,364,915; 5,238,892; 5,280,074; 5,288,473; 5,102,841; 4,956,426; 4,508,842; and EP Patent Nos. 0612753 and 0012147.

Optionally, the upgraded product is conducted away for storage or for further processing, such as conversion into polyethylene. This conversion may be performed in an ethylene polymerization unit that may include both the gas phase and solution polymerization methods, which conventional processes and may be employed in the practice of the present techniques. As an example, U.S. Pat. Nos. 6,822,057; 7,045,583; 7,354,979 and 7,728,084 describe different ethylene polymerization processes that may be utilized.

Optionally, the conversion product, such as ethylene, may be provided for other processes or used commercially as a product. These processes may include generating ethylene glycol or other products. As an example, the ethylene stream may be treated, separated and polymerized to form plastic compositions, which may include polyolefins, particularly polyethylene. Any conventional process for forming polyethylene may be used, while catalytic processes are preferred. Particularly preferred are metallocene, Ziegler/Natta, aluminum oxide and acid catalytic systems. Examples may include U.S. Pat. Nos. 3,258,455; 3,305,538; 3,364,190; 5,892,079; 4,659,685; 4,076,698; 3,645,992; 4,302,565; and 4,243,691. In general, these methods involve contacting the ethylene product with a polyolefin-forming catalyst at a pressure and temperature effective to form the polyolefin product.

Beneficially, hydroprocessing (which may specifically be hydrotreating) and using high-severity operating conditions in a thermal pyrolysis reactor provide greater flexibility in the feed utilized. That is, the feed may include a broader range of hydrocarbon feeds, which may have a resid content of ≥10 wt %, which may be cracked along with a hydrogen containing stream, such as methane or hydrogen. This hydrotreating provides a process for using non-volatile low hydrogen content feeds or feeds containing non-volatile, low hydrogen content fraction to be used as pyrolysis feeds. High-severity hydrotreating or hydrovisbreaking facilitates non-volatile conversion to a lighter volatile fraction, which results in more feed being cracked in the thermal pyrolysis reactor. Further, hydrotreating processes, such as hydrovisbreaking, may be employed to substantially increase the volatility of the hydrocarbon feed (e.g., resid conversion) without unnecessarily adding expensive hydrogen to perform aromatics conversion. Thus, hydrotreating processes that yield volatile, low hydrogen-content hydrocarbon products may be an acceptable feed to the present techniques. These low hydrogen content hydrocarbon feeds, which do not typically react in at low-severity condition or react to lower value products (e.g., dry gas or condensed aromatic rings), react in this process to provide $C_2U$. The high-severity operating conditions of the present techniques convert aromatic containing and/or methane containing feeds to valuable $C_2$ products at high levels. As such, the process may utilize a broad range of hydrocarbon feeds that foul or are unreactive in other process.

In addition, as noted above, by using high-severity conditions (e.g., higher temperatures) in the pyrolysis stage of the process, the present techniques may enhance $C_2$ selectivity. That is, the pyrolysis stage may crack the pyrolysis feed at residence times that are lower than other processes, such as low-severity processes. As a result, the pyrolysis feed is more efficiently cracked and the reactor size may be smaller (e.g., less capital expense and more efficient).

Further, the process may optionally involve other processing steps. For instance, the use of compressors depends upon the operating pressure of the thermal pyrolysis reactor and units within the recovery stage or downstream of the reactor. Also, the process may involve separation processes that remove various recycle products, such as methane and/or hydrogen, for example, from the remaining reactor product, which may form an acetylene-rich product and an acetylene-lean product. These processes may involve separating different products from the remaining reactor product in the recovery stage. The acetylene-rich product may include ≥50 wt % of the acetylene in the reactor product, ≥70 wt % of the acetylene in the reactor product, ≥85 wt % of the acetylene in the reactor product, or even ≥95 wt % of the acetylene in the reactor product. The acetylene-lean product may include from 0 wt % to the remaining portion of the acetylene that is not in the acetylene-rich product. The at least a portion of the reactor product may pass through one or more product separations, such as a light gas separation or a heavier separation, to remove different products from the remaining reactor product.

For example, after block 206, different light gas products (e.g., a portion of the light gas in the reactor product from the reactor) may be separated as light gas products and the remaining reactor product may form an acetylene-rich product. The light gas removal process may include different separation mechanisms along with a basic wash, for example caustic wash or amine scrubbing, to conduct the light gas products away from the at least a portion of the reactor product. For other embodiments, the light gas separation mechanisms may include pressure swing adsorption, membranes, cryogenic distillation, electrochemical separation, liquid absorption and/or liquid phase absorption and light gas desorbtion. The membrane inlet pressure or the pressure swing adsorption inlet pressure may be between 150 psig (1034 kPag) and 250 psig (1724 kPag), while the liquid phase absorption and light gas desorbtion may be performed at pressures between 50 psig (345 kPag) and 250 psig (1724 kPag). The light gas separation mechanisms may be used to separate hydrogen, carbon monoxide, methane, nitrogen or other light gases. The light gas products, such as hydrogen and/or methane, separated from the remaining portion of the reactor product may be used as a hydrogen containing stream in the thermal pyrolysis reactor or as the hydrogen containing stream in a hydrotreating unit, a feed stripping medium, as a fuel for the thermal pyrolysis reactor, or as a byproduct. The light gases may contain a fraction of the methane separated from the remaining reactor product or cracked stock. Further, in some embodiments, the light gas separation may include additional stages or units to remove one or more of carbon dioxide ($CO_2$), hydrogen sulfide ($H_2S$), and water ($H_2O$), but may also include other reactive impurities. In particular, carbon dioxide and hydrogen sulfide, if present, may be removed by washing the stream with a solution of alkali or a salt of an amine or organoamine. If water is present, it may be removed by a methanol treatment, such as described in Belgian Patent No. 722,895. Other methods for removing water are adsorption and extraction by diethylene glycol. Various exemplary embodiments of this process are described further below.

Optionally, after block 206, a heavy product separation process may be used to conduct away a product of condensables from at least a portion of the reactor product. The condensables may include vaporized liquids that condense, such as benzene, or are separated via cooled separations for example, adsorption, vapor liquid separators, flash drums etc. Certain exemplary embodiments of this process are described further below in FIGS. 3 and 4.

Figure 3:
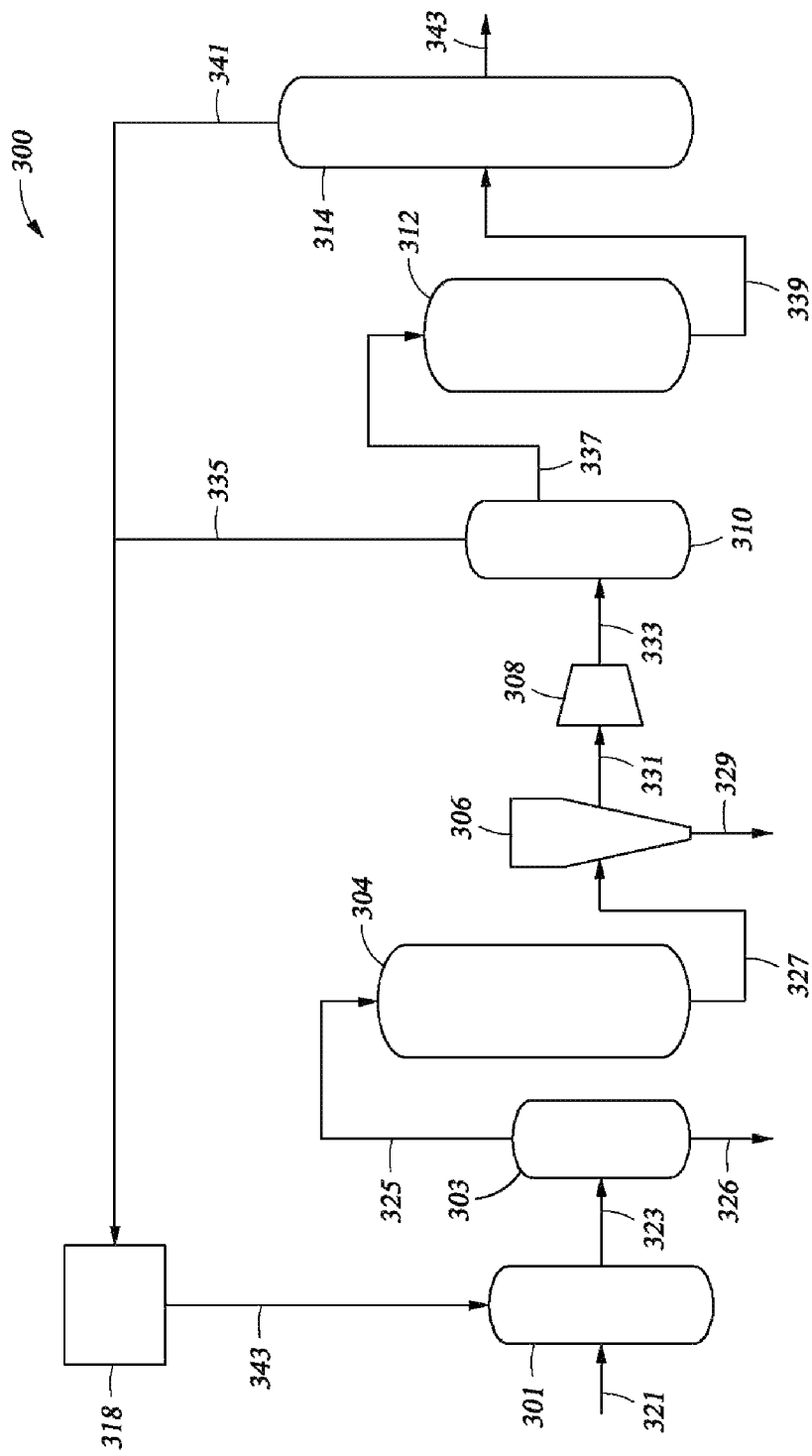
FIG. 3 is a simplified diagrammatic illustration of an exemplary process to convert a hydrocarbon feed into polyolefins in accordance with an embodiment of the present techniques.

FIG. 3 is a simplified diagrammatic illustration 300 of an exemplary process for converting hydrocarbon feed to polyolefins in accordance with an embodiment of the present techniques. In this illustration 300, a particular configuration of unit operations (i.e. units) are coupled together to convert a hydrocarbon feed, which may have a resid content of ≥10 wt %, to polyolefins. The feed preparation stage may include a hydrotreater 301, a heater 318 and a feed separation unit 303, while the cracking stage may include the pyrolysis reactor 304. The recovery stage may include a solids removal unit 306, a compressor 308, a product separation unit 310, an acetylene converter unit 312 and an upgrading unit 314. The process will now be explained in more detail.

A hydrocarbon feed is provided via line 321 to the hydrotreating unit 301. The hydrocarbon feed may have a resid content of ≥10 wt %, such as crude, atmospheric resid, vacuum resid, and/or other streams containing asphaltenes, for example. Along with the hydrocarbon feed, a hydrogen containing stream may be provided to the hydrotreater 301 via line 343. The hydrogen containing stream may include steam, methane, hydrogen or any combination thereof. The hydrotreater 301 may be any conventional hydrotreating process, such as U.S. Pat. Nos. 7,074,324 and 7,816,299 and U.S. Patent App. Pub. No. 2008/0067109. This hydrotreater may be configured to add hydrogen to break up heavy molecules, which includes using hydrogen to separate aromatic cores from each other without saturating the aromatic cores (e.g., hydro visbreaking). Again, as noted above, the extent of aromatic carbon conversion may be less than half of the extent of resid conversion, less than one-fourth of the extent of resid conversion or less than one-sixteenth of the extent of resid conversion.

After hydrotreating, the hydrotreated product is provided from the hydrotreater 301 via line 323 to the feed separation unit 303. The feed separation unit 303 may be used to separate the hydrotreated product into a vapor product and a solid/liquid product. Examples of equipment suitable for separating the vapor product from the solid/liquid product include a knockout drum (e.g., substantially any vapor-liquid separator), a flash drum, distillation column/unit, flash drum having a heating means within the drum, a knockout drum having heating means within the knock-out drum, and combinations thereof. During the separation, the temperature of the feed separation unit 303 is maintained between 50° C. and 750° C. or preferably between 100° C. and 515° C., which may be adjusted to control the separation level within the feed separation unit 303. Depending on the hydrotreated product, the vapor product (e.g., a portion of the hydrotreated product) may be readily separated from the remaining non-volatiles. Without separation, the solid/liquid product of the hydrotreated product may foul downstream lines or units. The solid/liquid product, which may include non-volatiles, may be withdrawn or removed from the feed separation unit 303 as a bottoms product or stream via line 326, which may be further processed or utilized for fuel for the thermal pyrolysis reactor 304 or other units, such as the compressor 308. The vapor product, which is a portion of the hydrotreated product, may be withdrawn from feed separation unit 303 as an overhead stream via line 325 and passed to the thermal pyrolysis reactor 304.

Optionally, a diluent may be provided via a line (not shown), which may include $H_2$, water or a lighter hydrocarbon (e.g., the lighter hydrocarbon is preferably a hydrocarbon with a hydrogen content that is greater than the hydrotreated product). The diluent may be added to the hydrotreated product prior to the thermal pyrolysis reactor 304 (e.g., to the hydrotreated product prior to the feed separation unit 303, to the hydrotreated product within the feed separation unit 303, or to the vapor phase after the feed separation unit 303).

The hydrotreated product, which may be the vapor portion of the hydrotreated product, may be the pyrolysis feed or may optionally be adjusted to form the pyrolysis feed depending if the hydrogen content of the portion of the hydrotreated product is within a predetermined range, as noted above. That is, a hydrogen containing stream may be mixed with the hydrotreated product from the feed separation unit 303 prior to the or at the thermal pyrolysis reactor 304 to form the pyrolysis feed. This adjustment may be made to have the pyrolysis feed include an atomic hydrogen to carbon (H/C) ratio of the combined hydrogen ($H_2$) and hydrocarbon of the pyrolysis feed in a range from 3 to 15, such as 3, 5, 6, 7, 8, 10, 15, or values in between, as noted further above.

The pyrolysis feed (e.g., portion of the hydrotreated product) may then be provided to the pyrolysis reactor 304 via line 325. Similar to the discussion above, the thermal pyrolysis reactor 304 may include any of a variety of reactors, which may preferably be a reverse flow regenerative reactor, and may be operated to produce a reactor product. Accordingly, the thermal pyrolysis reactor 304 may have different piping configurations to provide combustion feed (e.g., fuel) and the pyrolysis feed separately, depending on the specific configuration.

The reactor effluent or reactor product from the thermal pyrolysis reactor 304 is conducted away via line 327 to the solid removal unit 306 and other recovery stage units. The solid removal unit 306 may include water scrubbing, oil scrubbing, cyclone separation, electrostatic separation, filtration, and/or moving bed adsorption. As may be appreciated, each of these systems may be combined together in one or more units to overcome certain limitations within the system. For instance, water scrubbing is effective to remove solid carbon black and other solids, but it limits the recovery of heat in the effluent. Oil scrubbing may be utilized for heat recovery, but it may present problems with fouling and emulsion formation. Cyclone separation may be limited to remove solid carbon, but not other smaller or fine solids. Electrostatic separation may have problems with clogging and short-circuiting due to carbon deposit buildup. Adsorption and filtration are limited to handling small amounts of solids and may be problematic for larger amounts of solids. As a result, one or more of these techniques may be coupled together in series to provide the appropriate separation. The solid-liquid phase of the at least a portion of the reactor product may be conducted away from solid removal unit 306 as a bottoms product, which may be a bottoms stream, via line 329. The bottoms product may include carbon black, soots, and/or heavy aromatic oils and/or tars. If the bottoms product is "dry", it may be handled via filtration or electrostatic separation. If sticky or wet, it may be handled via washing (oil or water) or absorption. The bottoms product may be recycled to the thermal pyrolysis reactor or may be used as a fuel in the thermal pyrolysis reactor or for other units. The remaining reactor product may be withdrawn from solid removal unit 306 as an overhead stream via line 331 and passed to the compressor 308.

The compressor 308 may receive the remaining reactor product from the solid removal unit 306 and compress the product to provide a compressed product via 333 to the product separation unit 310. The compressor 308 may compress to the vapor product to a pressure from 50 psig to 400 psig (345 kPag to 2758 kPag), or more preferably from 150 psig to 300 psig (1034 kPag to 2068 kPag). For other embodiments, the pressure may be adjusted for hydrogen ($H_2$) removal (e.g., pressure swing adsorption, hydrogen membrane and/or cryogenic distillation, electrochemical separation) and acetylene hydrogenation.

Once compressed, different products, such as different light gases or heavy products may be separated from at least a portion of the reactor product in the product separation unit 310. The product separation unit 310 may include the different units discussed above, which may also include steps to remove different products (e.g., $CO_2$, $H_2S$ and/or $H_2O$) from the process. For instance, carbon dioxide can be removed by washing the reactor product. This step may also include drying to remove entrained water. The acetylene rich product may be recovered from the product separation unit 310 via line 337 and passed to the acetylene converter 312, while the recycle products, such as hydrogen and/or methane, may be withdrawn as the hydrogen containing stream via line 335.

Optionally, the acetylene converter 312 may receive at least a portion of the reactor product (e.g., acetylene-rich product or $C_2U$ products comprising acetylene and ethylene) from the product separation unit 310. The acetylene converter (A/C) selectively hydrogenates the acetylene to ethylene without significantly hydrogenating the ethylene to ethane. The acetylene converter may operate at feed levels ranging from 0.5 to 15 mol % acetylene. The acetylene converter may operate at pressures from 32 psig (221 kPag) to 400 psig (2758 kPag), at inlet temperatures of 50° C. to 300° C. and may utilize catalyst comprising group VI or VIII catalysts. Conversion levels for the hydrotreater may range from 70 wt % to 100 wt % acetylene conversion and may have selectivity to ethylene from 70 wt % to as high as 98 wt % to ethylene. The acetylene converter 312 may include an optional finishing acetylene converter to convert remaining levels of acetylene at 100 wt % conversion of the acetylene. This finishing acetylene converter may be in fluid communication with the one or more units, such as the acetylene converter 312 or other units downstream of the acetylene converter 312. The acetylene converter 312 may include a hydrogenation unit, and optionally may further include a compressor, stream recycle components, desorption unit and/or separation unit.

In one embodiment, a conversion product of ≥50 wt % of ethylene may be conducted away from the acetylene converter 312 to storage or for further processing. As an example, the conversion product may be passed to the upgrading unit 314 via line 339. The upgrading or purification unit 314 may include a demethanator tower (to remove $H_2$, $CH_4$, $N_2$ and CO) and a $C_2$ splitter to remove ethane and upgrade ethylene to polymer grade ethylene. The upgrading unit 314 may also include $C_2$ or $C_3$ refrigeration train, compression and additional distillation towers. This unit may separate the conversion product from the acetylene converter 312 into one or more products and an upgraded product, such as an ethylene stream. The one or more products, which are provided to line 341, may include different light gas products (e.g., hydrogen, carbon monoxide, nitrogen, methane, and the like) or heavy products (e.g., ethane and $C_{3+}$ streams). A portion of the recovered products may be recycled for processing again in the thermal pyrolysis reactor, such as methane and/or hydrogen. Further, if the upgraded product is an ethylene stream, the upgrading unit 314 may also include an ethylene polymerization unit. The ethylene polymerization unit may be a catalytic reactor, which may include a gas catalyst and/or a liquid catalyst.

The process may involve a catalyst, solvent and the feed stream, as discussed above. Regardless, the upgraded product may be provided via line 343 for storage or further processing.

In some embodiments, a portion of the acetylene in the reactor product may optionally be combined with other process steps to form other products. In particular, the portion of the acetylene may be an intermediate product or precursor in a process within a chemical plant, in route to other preferred products, such as vinyl esters, ethylene, acetaldehyde, propanal, propanol, acrylic acid, and/or the like.

The hydrogen containing stream, which may be drawn from the product separation unit 310 or the upgrading unit 314, may be provided to the heater 318. The heater may be a heat exchanger, boiler or furnace, or other suitable unit. The heater 318 may be used to heat the hydrogen containing stream to temperatures from 300° C. to 500° C., preferably 375° C. to 425° C. Further, the hydrocarbon feed may also be preheated to a similar temperature.

This configuration provides an enhanced process for processing hydrocarbon feeds that have higher boiling point fuel oils and converts these feeds into lower average molecule weight stream. That is, the process takes a lower value feed having a higher average boiling curve and converts the feed into chemical products, such as ethylene, instead of using these feeds as fuel. As a result, combustible non-volatiles may be converted into volatiles and thereby utilized as a pyrolysis feed for this process.

Figure 4:
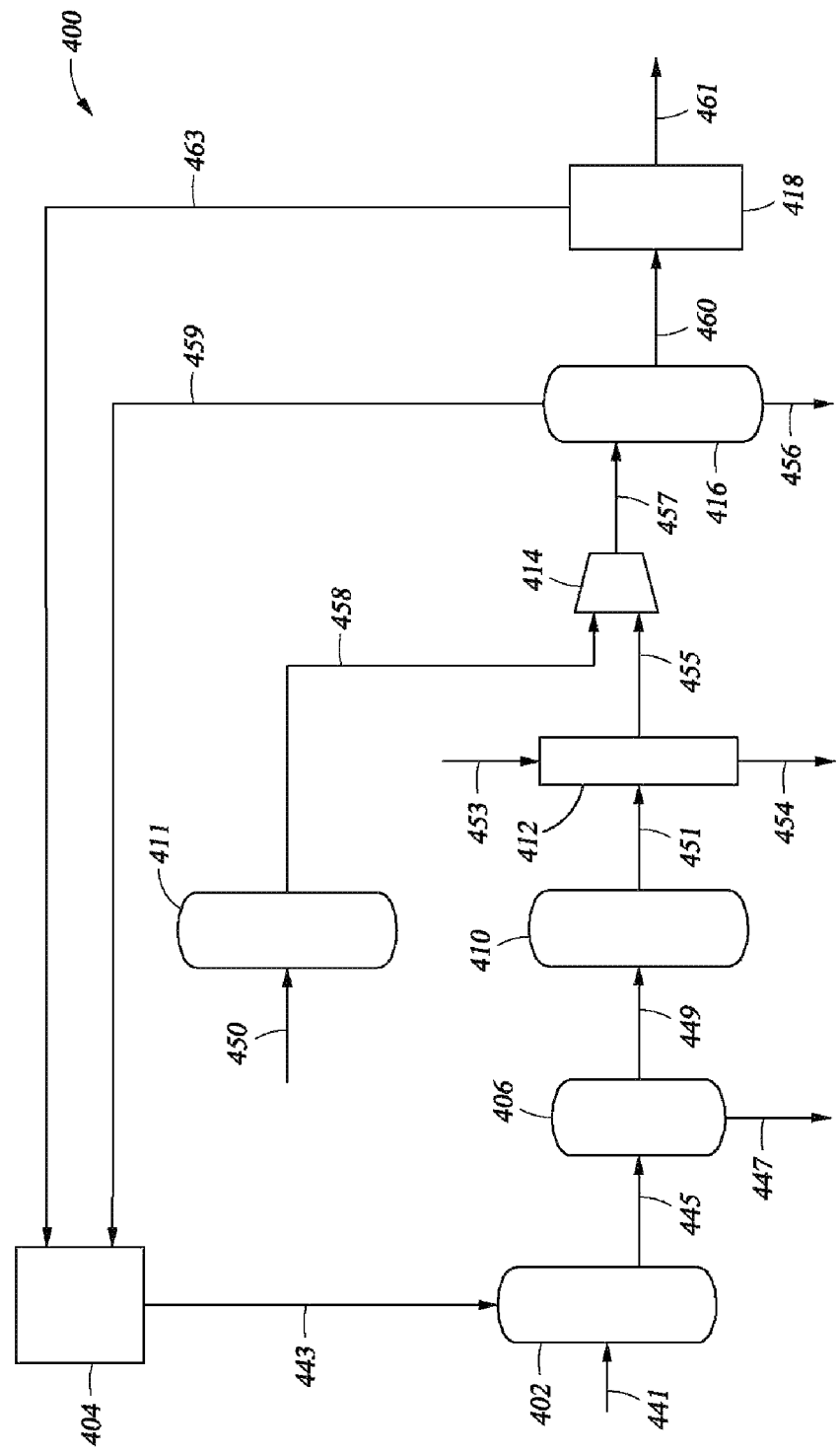
FIG. 4 is a simplified diagrammatic illustration of another exemplary process to convert a hydrocarbon feed into polyolefins in accordance with an embodiment of the present techniques.

FIG. 4 is a simplified diagrammatic illustration of another exemplary process to convert a hydrocarbon feed, such as atmospheric bottoms or resid, to a product, such as polyethylene, in accordance with an embodiment of the present techniques. In this illustration 400, a particular configuration of units is coupled together to convert a hydrocarbon feed into polyolefins, which is further integrated with another pyrolysis reactor of the same or a different type. This configuration includes a hydrotreating unit 402, a feed separation unit 406, a first pyrolysis reactor 410, a second pyrolysis reactor 411 and recovery stage. The recovery stage of this process may include a heat exchanger 412, a compressor 414, a product separation unit 416, and a recovery unit 418. Again, similar to the discussion related to FIGS. 2 and 3, various units in this configuration may operate and function in a substantially similar manner to the units noted above in FIGS. 2 and 3.

To begin, the hydrocarbon feed, such as fuel oil (e.g., atmospheric resid) or other suitable hydrocarbon feed, is provided via line 441 to the hydrotreating unit 402 along with a hydrogen containing stream provided via line 443 from the heater 404. The hydrotreating unit may involve both thermal and catalytic hydrotreating and may be operated at pressures from 100 psig to 3000 psig (689 kPag to 20684 kPag), or between 200 psig and 800 psig (between 1379 kPag and 5516 kPag). The hydrotreating unit may operate at temperatures from 250° C. to 500° C. (preferably above 375° C. and below 450° C.) to promote incipient cracking (e.g., maximize conversion of material boiling above 565° C.). The hydrotreating unit 402 may include hydrodemetallation reactor to remove non-combustibles from the process. The hydrotreating unit may also contain a high pressure let down drum and optional low pressure let down drum before providing hydrotreated product to the feed separation unit 406 via line 445. The heater 404, which may be similar to the heater discussed above in FIG. 3, may be used to heat the hydrogen containing stream prior to the hydrotreating unit 402. The feed separation unit 406 may divide the hydrotreated product into a vapor product (e.g., the pyrolysis feed) provided to the first pyrolysis reactor 410 and a bottoms product that is conducted away from the process via line 447.

The first pyrolysis reactor 410 includes a thermal pyrolysis reactor, which may preferably include a reverse flow regenerative reactor. At least a portion of the reactor product from the pyrolysis reactor 410 may be passed to one or more heat exchangers, such as heat exchanger 412 via line 451. The heat exchanger 412 may use indirect heat transfer to cool at least a portion of the reactor product and minimize the addition of contaminates. In this embodiment, the reactor product from the reactor may pass through the process side of the heat exchanger 412, while a utility fluid may be provided via lines 453 and exit via line 454 out the heat exchanger. To minimize contamination, the reactor effluent may be maintained separate from the utility fluid, which is conducted away and may be used in other processes. Optionally, at least a portion of the reactor product may be further processed in the solid removal unit (not shown), similar to FIGS. 2 and 3.

A second pyrolysis reactor 411 is integrated with the recovery stage of the first pyrolysis reactor 410. The second pyrolysis reactor 411 may receive a second pyrolysis feed 450, which may include a liquid hydrocarbon feed or vapor hydrocarbon feed. The second pyrolysis reactor 411 may include a pyrolysis reactor of the same type or a different type, such as a steam cracking furnace, regenerative reverse flow reactor or other suitable reactor. Exemplary steam cracker furnaces and regenerative reverse flow reactor may include those noted above. The reactor types may include high-severity partial combustion, high-severity indirect combustion, high-severity arc process, high-severity thermal pyrolysis, low-severity partial combustion, low-severity indirect combustion, low-severity arc process, and/or low-severity thermal pyrolysis.

Regardless, at least a portion of the first reactor product and at least a portion of the second reactor product may be provided to a compressor 414 via lines 458 and 457, respectively. These reactor products may be combined within the compressor 414 or prior to the compressor in a combining unit, which may be a manifold, vessel or joint between the lines from the units. The compressor 414 may pressurize at least a portion of the reactor products to form a compressed product, which may be similar to the discussion above. The compressed product may be further processed in the product separation unit 416 to separate different products, such as hydrogen, methane or other products, as noted above in FIGS. 2 and 3. These products may be conducted away from the process via line 456 or may be provided via line 459 to the heater 404. The remaining reactor product may be processed in the recovery unit 418 to provide one or more products via line 461. The recovery unit 418, which may separate and convert various products, may include an acetylene converter and upgrading unit, as noted above. Further, different recycle products may be also separated in the recovery unit 418, which may be provided via line 463 to the heater 404. These different products may include hydrogen, methane or other products, as noted above in FIGS. 2 and 3.

Beneficially, this configuration provides a more efficient process to recover olefins by integrating different pyrolysis reactor types. For instance, in this configuration, one of the enhancements is the flexibility in the feed utilized for olefin recovery. That is, any hydrocarbon feed provided may be separated into different streams for the first pyrolysis reactor 410 and the second pyrolysis reactor 411. In particular, the first pyrolysis reactor 410 may be provided a low hydrogen content feed via line 441, while the second pyrolysis feed provided via line 450 may be removed in a distillation or separation step. As a specific example, an existing low-severity pyrolysis reactor and associated units may typically crack crude fractions, such as naphthas or gas oils, but if coupled with a high-severity pyrolysis reactor, waste streams or fuel streams, such as aromatic fuel oils, may be further cracked to chemical products in the first pyrolysis reactor 410 at high-severity operating conditions. Various combinations of different pyrolysis reactors may be envisioned, where each type of pyrolysis reactor may most efficiently crack a preferred portion of the hydrocarbon feed. As such, a group of pyrolysis reactors may be coupled together with each associated with different portions of the hydrocarbon feed.

As an exemplary configuration, the first pyrolysis reactor 410 may be a reverse flow regenerative reactor (e.g., a high-severity thermal pyrolysis unit), while the second pyrolysis reactor may be a steam cracker (e.g., a low-severity pyrolysis unit). A hydrocarbon feed, such as crude oil or fractions thereof, may be provided to a feed separation unit (not shown). The lighter fraction may be provided to the steam cracker to convert that portion to ethylene, while the heavy fraction may be provided to the hydrotreater 402. A portion of that heavy fraction may be provided to the reverse flow regenerative reactor for conversion into acetylene and ethylene. Naphtha and distillates are preferentially cracked in a liquid steam cracker at conditions to yield high levels of ethylene. The steam cracker may include a recovery section that comprises a TLE or quench, tar/solids removal, compression, separation, acetylene conversion and several purification steps. However, the heavy fractions, which include aromatic gas oils, for example, may be preferentially hydrotreated and cracked in the high-severity pyrolysis reactor to yield a first reactor product comprising acetylene and ethylene. At least a portion of the first reactor product may be in fluid communication with additional processing steps such as solid removal, compression or acetylene conversion, or may be processed or integrated with the existing liquid steam cracker recovery steps.

In one or more embodiments, the hydrocarbon feed may include different hydrocarbon mixtures thereof. The present techniques and compositions may be utilized with liquid feeds, such a vacuum resid or crude, for example. In one or more embodiments, the hydrotreated product is advantageously pyrolyzed with an overall hydrogen content of the hydrocarbon in the pyrolysis feed ≥10 wt %, preferably ≥12 wt %, and more preferably ≥15 wt %. Further, in other embodiments, the hydrocarbons in the pyrolysis feed may be a mixture of heavy hydrocarbon feed and methane, having aggregate hydrogen content ≥15 wt %. This adds the flexibility of controlling the $H_2$ byproduct. If $H_2$ is valued at a fuel/feed value, a lower hydrogen content feed may be used to maximize the chemical product value; or if $H_2$ is valued at chemical value (methane steam reforming value), higher hydrogen content feeds may be preferred (to meet chemical value $H_2$ demand).

Although the units of FIGS. 3 and 4 are shown as respective single and separate units, each of these units can alternatively comprise a plurality of units. For example, a separation unit may include more than one knockout drums, separators, and/or flash drums. Accordingly, different embodiments may utilize different units in this manner. Further, some additional embodiments, which are discussed further below, may be utilized in these embodiments of FIGS. 2 to 4.

In certain embodiments, the thermal pyrolysis reactor may be operated at different pressures to further enhance the operation of the system. For example, in some embodiments, the pyrolysis of volatized hydrocarbons may occur at different pressures, such as pressures ≥4 psig (27 kPag), ≥15 psig (103 kPag), ≥36 psig (248 kPag), ≥44 psig (303 kPag) or ≥103 psig (710 kPag), but the pressures may be ≤300 psig (2068 kPag), ≤163 psig (1124 kPag), or ≤150 psig (1034 kPag), or different combinations thereof. Pressures higher or lower than that disclosed above may be used, although they may be less efficient.

Each of the thermal pyrolysis reactors may be operated at different temperatures based on the specific operation and process variations. The different thermal pyrolysis reactors may include specific mechanisms and processes to heat the pyrolysis feed. Accordingly, each reactor may include different means for measuring the temperature of that specific process. As a specific example for a thermal pyrolysis reactor, the pyrolysis stream is heated by a solid material, which is heated by a combustion reaction. Usually, the solid material forms the channels that the pyrolysis stream travels through. The combustion reaction of combustion feed that heats the solid material may heat via convective and/or radiative mechanisms. In these reactors, the highest temperatures are observed in the stream that is heating the solids (e.g., combustion stream). At any location, the solid material has a temperature that is lower than that of the combustion stream from which it receives heat, while the pyrolysis stream being heated by the solid material has a temperature that is lower than the solid material. The specific temperature of the combustion stream, pyrolysis stream or solid material depends on its location within the reactor and on the configuration and/or operation of the pyrolysis reactor.

In certain thermal pyrolysis reactors (e.g., steam cracking furnace configuration), the heating and the pyrolysis process occur simultaneously, for example with a combusting stream on one side of partition (typically a wall or tubular) and the pyrolysis stream on the other side. Such reactors operate at or near steady state. The partition between the combustion feed and the pyrolysis feed has real physical dimensions and the temperature is not equal at every location. For example, on the combustion side, temperatures may be hottest near a flame region, and on the pyrolysis side temperatures increase with heat addition until some maximum temperature is reached. Steady state in these systems means that, at any given location relative to the fixed partition, temperatures remain relatively steady. However, the gases that travel through the reactor are heated and cooled by the chemistry and heat transfer that takes place in the reactor. The term "peak pyrolysis gas temperature" means the maximum temperature achieved by the bulk pyrolysis stream gases as they travel through the pyrolysis reactor (e.g., cracking region or radiant region). One skilled in the art will appreciate that temperatures immediately proximate to the partition may be higher, and may, in some infinitesimal layer, actually approach the solid temperature. However, the pyrolysis temperature referred to herein should be considered a bulk gas temperature, which is a temperature that could be measured by a device (such as a thermocouple) that is not in contact with the solid material. For example, if the gas is traveling through tubulars in a thermal pyrolysis reactor, the bulk gas temperature may be taken as the average temperature over any tubular cross-section, and the peak pyrolysis gas temperature as the highest cross-sectional-average temperature of the pyrolysis stream.

In a thermal pyrolysis regenerative reactor system, the heating and pyrolysis occur in sequential steps. First, a heating step, usually a combustion reaction or combustion step, is used to heat the solid material. Second, a pyrolysis step is carried out that absorbs heat from the solid material to effect a chemical reaction. The solid material may be in fixed orientation or in moving orientation. If moving, the solid is typically moved from a heating region to a pyrolysis region. Moving-solid systems appear to be step-wise from the perspective of the moving solid, however the gas streams may be at steady state in any absolute location, and temperatures are defined very much as discussed for thermal pyrolysis furnace-type reactors. When the solid material is in fixed orientation, a regenerative system may use valves to alternate introduction of pyrolysis and heating streams into the solid-containing region. The solid material may be designed to facilitate the process of heat addition and removal. Checker bricks, tiles and monoliths may be used as the solid materials within the reactor. Such materials form a network of passages that are used by the gases in each step to transit the region containing solid material. The heat addition step leaves a profile of temperatures in the solid material, that is, a temperature that varies along the path by which the gases transit the solid material. The shape of that profile depends on many factors, including if and where a heat release (combustion) reaction occurs, the initial temperature distribution, the duration of the heating step, the flow rate and inlet temperature of the gas stream, and the heat capacity and transfer properties of the gas and solid material. On average, the solid material is hottest at the end of the heating step. The pyrolysis step consumes heat and reduces average solid material temperature. The pyrolysis step changes the profile of temperatures in the solid material, in a way that depends on many factors, including where the heat consumption (pyrolysis) reaction occurs, the initial temperature distribution, the duration of the pyrolysis step, the flow rate and inlet temperature of the gas stream, and the heat capacity and transfer properties of the gas and solid. Fixed-solid regenerative pyrolysis reactors are not at steady state. That is, at any given location, the temperature changes. However, these reactors may be in a periodic steady state, meaning that the same cycling of temperatures occurs over and over as the reactor oscillates between heating and pyrolysis.

In a reverse-flow regenerative system, a reversal occurs in the direction of transit of the gases through the region that contains the solid material, and this reversal occurs in between the heating (e.g., combustion) and pyrolysis steps. In some embodiments, reversal occurs between every step, and in other embodiments reversal occurs in alternating step changes. Regardless, the flow reversal enables substantial heat exchange between the incoming gas of one step and the outgoing gas of the alternate step. This results in a reactor that has highest temperatures near the middle of the flow path, and relatively cool temperatures at both ends of the reactor.

In a regenerative pyrolysis system, peak pyrolysis gas temperature is determined as follows. The peak pyrolysis gas temperature typically is experienced by the gases at the beginning of the pyrolysis step, because the solid material is typically at its highest temperature at the beginning of the pyrolysis step. One skilled in the art will appreciate that temperatures immediately proximate to the solid material may be higher, and may, in some infinitesimal layer, actually approach the solid temperature. However, the pyrolysis temperature referred to herein should be considered a bulk gas temperature, which is a temperature that may be measured by a device (such as a thermocouple) that is not in contact with the solid material. For example, if the gas is traveling through channels in a checkerbrick, tile or honeycomb solid material, the bulk gas temperature could be taken as the average temperature over any channel cross-section, and the peak pyrolysis gas temperature as the highest cross-sectional-average temperature of the pyrolysis stream.

Thermal pyrolysis reactors may also be characterized in terms of the residence time of pyrolysis gases in the reactor. Residence time is most generally defined as the time required for some average non-reacting molecule to pass through the pyrolysis reactor or furnace. Residence time may be further defined to be the time spent within the actively heated or cooled portions of the reactor or furnace. This includes time spent within tubulars or heat transfer solids of a furnace or regenerative reactor, respectively, but excludes residence time spent in headers or other means of conveyance to or from the actively heated or cooled regions of the furnace or reactor. Additionally, the high-severity residence time is defined as the time that pyrolysis stream components are exposed to temperatures above the severity threshold. An exact calculation of residence time requires measurements with tracer compounds (such as radioactive additives to the feed) or requires a specific knowledge of the temperature and composition of the pyrolysis stream at all times as it passes through the pyrolysis reactor. For the purposes of the present application, residence time (in either form) may be approximated using interpolation and extrapolation of discreet composition and temperature measurements, and/or using model-based estimations of temperature and composition, as is known in the art.

In addition to the operating pressure, the one or more embodiments may include the conversion of feedstocks into higher value hydrocarbons, such as acetylene, at different temperatures. These temperatures may include high pyrolysis temperature, which in the past has been a significant barrier to commercialization and efficiency. The high severity thermal pyrolysis reactor according to the present techniques is a higher temperature hydrocarbon pyrolysis reactor that operates at higher temperatures than steam cracking reactors used in commercial steam cracking operations. For example, naphtha steam cracking operations typically operate at furnace radiant coil outlet temperatures of ≤about 815° C., which corresponds to the peak pyrolysis gas temperature. However, in the present techniques, the high severity thermal pyrolysis reactor may operate at peak pyrolysis gas temperatures between 1200.0° C. and 2200.0° C., preferably between 1400.0° C. to 1900.0° C. In particular, for reactors with an isothermal heat profile, the temperatures may be between 1450° C. and 1700.0° C., or between 1540.0° C. and 1650.0° C. For reactors with a Gaussian like heat profile, the peak pyrolysis gas temperatures may be in the range of 1540° C. and 2200.0° C. or 1600.0° C. and 1800.0° C. In some reactions, it may even be still more preferable to expose the pyrolysis feed to heat using very short residence times, such as ≤0.1 second, to a temperature in excess of 1600.0° C. Pyrolysis reactions that benefit from reaction or conversion of methane that may be a part of the pyrolysis feed, typically involve peak pyrolysis gas temperatures in excess of 1400.0° C. for the methane to react or convert. An exemplary preferred process may pyrolyze the feed stream within the reactor, such as at peak pyrolysis gas temperatures of from 1500.0° C. to 1900.0° C., and more preferably from 1600.0° C. to 1800.0° C. Exemplary residence times preferably may be short, such as ≤0.5 second, ≤0.3 second and preferably ≤about 50 milliseconds or in the range of 0.5 seconds to 0.001 seconds. High severity residence times are preferably ≤0.05 seconds, and more preferably ≤0.02 seconds.

As described earlier, achieving any peak pyrolysis gas temperature involves the existence of a solid temperature that is heated to a higher temperature, and a combustion gas temperature that is a higher temperature than the solid temperature. In one or more embodiments of the present techniques, the maximum temperature of the solid elements in the thermal pyrolysis system (e.g., tubulars for furnaces or heat transfer solids for regenerative systems) is between about 5° C. and about 500° C. higher than the peak pyrolysis gas temperature. In a preferred embodiment, the maximum temperature of the solid elements in the thermal pyrolysis system is between 10° C. and 100° C. higher than the peak pyrolysis gas temperature. Reverse flow regenerative reactors may also include some amount of quenching by means of heat removal to the heat transfer solids. In reverse flow regenerative reactor embodiments of the present techniques, the pyrolysis gas may be cooled to a temperature between 100° C. and 1000° C. by means of heat removal to the heat transfer solids in the reactor, and more preferably cooled to a temperature between 300° C. and 550° C.

As example, U.S. Patent App. Ser. No. 61/226,499, which is incorporated by reference, describes a process and regenerative pyrolysis reactor utilized for pyrolyzing a resid-containing hydrocarbon feedstock. These process steps and/or pyrolysis reactor may be utilized in one or more of the embodiments described above. For instance, this process may include (a) feeding a resid-containing hydrocarbon feedstock to a thermal cracking unit; (b) thermally cracking at least 60 wt % of the resid having a boiling point of at least 565° C. in the hydrocarbon feedstock to form a vapor phase containing cracked hydrocarbons, based upon the total weight of the hydrocarbon feedstock having a boiling point of at least 565° C.; (c) separating the vapor phase from remaining non-volatiles; and (d) converting the separated vapor phase in a regenerative pyrolysis reactor system into a pyrolysis product.

In other embodiments, the thermal pyrolysis reactor may be a regenerative reverse flow reactor or regenerative pyrolysis reactor. Regenerative pyrolysis reactors are well suited for processing volatized or volatilizable feedstocks that are substantially free of non-volatile components, such as metals, and other residual or nonvolatilizable components, which would otherwise lay down, ash, and/or build up in the reactor. Examples of such reactors may be found in U.S. Patent App. Pub. Nos. 2007/0144940 and 2008/0142409. Other examples may be found in U.S. Patent App. Pub. No. 2009/0008292 and 2009/008292; U.S. Pat. No. 7,491,250 U.S. Patent App. Pub. No. 2009/008292; and U.S. Patent App. Ser. No. 61/349,464, which are each incorporated by reference.

As an example, U.S. patent application Ser. No. 11/643,541 (U.S. Patent App. Pub. No. 2007/0191664), which is incorporated by reference, describes a process and high severity regenerative thermal pyrolysis reactor utilized to manufacture acetylene from a methane or hydrocarbon-containing feed. These process steps and/or pyrolysis reactor may be utilized in one or more of the embodiments described above. For instance, the process may include a reactor system that includes (i) a first (quenching) reactor comprising a first end and a second end, and (ii) a second reactor comprising primary end and a secondary end, the first and second reactors oriented in a series relationship with respect to each other such that the secondary end of the second reactor is proximate the second end of the first reactor. The process may include a two-step process wherein heat is (1) added to the reactor media via in-situ combustion step and (2) removed from the reactor media via in-situ endothermic pyrolysis step. The combustion step may involve passing a first and second combustion reactant (combustion feeds) separately but simultaneously through the first (quenching) reactor, by supplying a first reactant through a first channel in the first reactor and supplying at least a second reactant through a second channel in the first reactor, such that the first and second reactants are supplied to the first reactor from the first end of the first reactor. The combustion step may further involve combining the first and second reactants at the second end of the first reactor and reacting the combined reactants to produce a heated reaction product; passing the heated reaction product through the second reactor to transfer at least a portion of the heat from the reaction product to the second reactor, and recovering an exhaust gas from the second reactor. Preferably, the combining is enhanced by a reactant (combustion feed) mixer that mixes the reactants to facilitate substantially complete combustion/reaction at the desired location, with the mixer preferably located between the first and second reactors. Thereafter, the endothermic pyrolysis step, which may be carried out at a pressure between about 5 pounds per square inch absolute (psia) (35 kPa absolute (kPaa)) up to about 45 psia (310 kPaa), supplies methane or other hydrocarbon through the heated second reactor to the first reactor, in flow direction the opposite to that of the heating (combustion) step, to convert at least a portion of the methane into acetylene; passing the supplied methane and the produced acetylene through the first reactor to quench the methane and the produced acetylene; and recovering the produced acetylene. The process may further include supplying hydrogen in the second reactor during the pyrolysis step to moderate the reaction of the methane or other hydrocarbons in the feed. Hydrogen may be used in molar ratio to methane of 0 to 5, preferably of 1 to 3 during the pyrolysis step. In a preferred embodiment, the media in the first reactor includes one or more honeycomb monolith structures that provide flow channels for the first and second reactant. The process may further include media of the first or second reactor that has wetted surface area between 50 and 3000 ft$^{-1}$, heat transfer coefficient ≥0.02 cal/cm$^3$s° C., and bulk heat capacity ≥about 0.10 cal/cm$^{3}$° C., and may be comprised of honeycomb monoliths having 40 to 80% open frontal area and between about 50 and 2000 channels per square inch. The process may further include compressors, blowers, or fans to supply air as one combustion feed during the combustion step, which may be carried out at a pressure between about 15 psia (103 kPaa) and 45 psia (310 kPaa); may include expansion turbines to recover mechanical energy from higher pressure exhaust gases; and may include recycle of exhaust gases (EGR) to the combustion feed for combination with the air, for example to reduce the oxygen content and the adiabatic flame temperature of the combustion feed. Noncombustible gases, for example $H_2O$, $CO_2$, and $N_2$, may be added to the combustion feed to reduce combustion temperature. The combustion step may comprise a first and second reactant that are a fuel gas and an oxidant that are maintained substantially separated as they pass through the first reactor and which combust or burn when combined. By substantially separated is meant that at least 50%, and more preferably 75% or 90% of the potential combustion that may occur after the axial transit of the first reactor. The process may further include a mixer that is comprised of multiple mixer segments, each preferably having similar cross-sectional area and length and each preferably accepting flow during the combustion step from roughly equal numbers of first and second channels, representing roughly equal proportions of first and second reactant, and having a characteristic L/D between 0.1 and 5.0. Preferably, the mixer has a total volume ≤20% of the total volume of mixer plus flow regions in first and second reactor, and preferably has a geometric void volume ≤20% of the void volume in mixer plus first and second reactor. The process may further include a cycle time that includes the time spent in combustion step plus time spent in pyrolysis step plus any time needed to switch between steps. Typical cycle times may be between 1 and 240 seconds, or between 2 and 60 seconds, and without expectation that combustion and pyrolysis steps have equal durations.

Optionally, in one or more embodiments, at least a portion of the hydrocarbon feed comprises biological matter and/or hydrocarbon derived from biological matter. Biological matter can be converted into useful products via biochemical processes (e.g., fermentation) or thermochemical processes (e.g., gasification). As the biochemical processes is a slow process as compared to thermochemical processes, the thermochemical processes are typically utilized to process biological matter. The thermochemical processes typically produce syngas (used to produce hydrocarbon fuel) and bio oil, which may include tar, and ash. The syngas is typically used to produce hydrocarbon products, while the bio-oil is used for fuel because the bio-oil contains a relatively high tar content. The process of the invention is advantageous because it can utilize the relatively low-value bio-oil as (i) hydrocarbon feed and/or (ii) fuel, e.g., when a regenerative reactor is utilized for the pyrolysis.

Accordingly, in one or more embodiments, the thermal process described above may be utilized to enhance the processing of biological matter. In these embodiments, the biological matter may be utilized to produce a biofeeds that has molecules (and mixtures thereof) including both carbon atoms and hydrogen atoms, and optionally including other atoms (heteroatoms) such as oxygen, sulfur, and nitrogen, wherein the carbon atoms and hydrogen atoms together comprise ≥75.0% of the atoms present in the molecule or mixture of molecules; but including molecules comprising in the range of 10.0 atom % to 60.0 atom % of oxygen atoms.

In these embodiments, biological matter may be provided to one or more gasification units that are in fluid communication with and upstream of a hydrotreating unit (e.g., hydrotreating unit 301 or 402) and/or upstream of reactor 304 or 410. The gasification unit may convert the biological mater into a vapor fraction that includes carbon dioxide and hydrogen and a liquid fraction that includes biofeeds and solids, such as char and ash. The solids may be conducted away from the remaining feed in a feed separation unit (e.g., feed separation unit 303 or 406) upstream of the reactor 304 or 410. Because of the high severity operating conditions of the reactor 304 or 410, the hydrocarbons with the biofeed may be efficiently converted into useful products that may be separated from the effluent, as noted above.

As an example, the biological matter conversion process may include converting a biological matter into a vapor fraction and a liquid fraction having a hydrogen content below 12 wt %; deriving a pyrolysis feed from the liquid fraction, wherein the pyrolysis feed comprises hydrocarbons that contain one or more heteroatoms that comprise ≥10 atom % of the atoms present in hydrocarbons; and exposing the pyrolysis feed a temperature in the range of 1540° C. to 2000° C. in a first region under thermal pyrolysis conditions to produce a reactor products, the reactor products comprising molecular hydrogen, carbon monoxide, and ≥1.0 wt % of $C_2$ unsaturates based on the weight of the reactor product. This method may also include converting ≥10.0 wt. % of the reactor products' $C_2$ unsaturates, based on the weight of the reactor products' $C_2$ unsaturates, to form a product comprising ≥1.0 wt. % of $C_{3+}$ aldehyde and/or ≥1.0 wt. % $C_{3+}$ alcohol based on the weight of the product. Further, the liquid fraction may include heteroatoms that are oxygen, nitrogen, sulfur; and the heteroatoms may include 10 to 60 atom % in the hydrocarbon. The method may include deriving a pyrolysis feed from the liquid fraction (e.g., pyrolysis oil), the pyrolysis feed comprising hydrocarbon containing at least one or more of oxygen and nitrogen; and exposing the hydrocarbons in the pyrolysis feed a temperature in the range of 1540° C. to 2000° C. in a first region under thermal pyrolysis conditions to produce a reactor product, the reactor product comprising molecular hydrogen, carbon monoxide, and ≥1.0 wt % of $C_2$ unsaturates based on the weight of the reactor product. Also, the method may include converting ≥10.0 wt. % of the second mixture's $C_2$ unsaturates, based on the weight of the reactor products' $C_2$ unsaturates, to form a product comprising ≥1.0 wt. % of $C_{3+}$ aldehyde and/or ≥1.0 wt. % $C_{3+}$ alcohol based on the weight of the product.

The embodiments of the present techniques may also comprise different embodiments, such as in the following exemplary paragraphs:

1. A method for processing hydrocarbons comprising: contacting hydrogen ($H_2$) and a hydrocarbon feed containing ≥10.0 wt % resid in the hydrocarbon feed with a catalyst to form a hydroprocessed product; exposing a pyrolysis feed derived from the hydroprocessed product at high-severity thermal pyrolysis operating conditions to produce a reactor product that comprises hydrogen, ethylene and acetylene; and separating at least a portion of the hydrogen ($H_2$) from the reactor product, wherein the hydrogen ($H_2$) contacting the catalyst comprises at least a portion of the separated hydrogen ($H_2$).

2. The method of paragraph 1, wherein the reactor product has a $C_{3+}$ to acetylene weight ratio ≤0.45.

3. The method of paragraphs 1 or 2, wherein ≥20.0 wt % of the resid is converted to components having a normal boiling point <565° C.

4. The method of paragraphs 1 or 2, wherein ≥50.0 wt % of the resid is converted to components having a normal boiling point ≤565° C.

5. The method of paragraphs 1 or 2, further comprising removing combustible non-volatiles and/or non-combustible non-volatiles from the hydroprocessed product, the hydroprocessed product comprising ≤5.0 wt % of the combustible non-volatiles and ≤2 ppmw of the non-combustible non-volatiles based on the weight of the hydroprocessed product.

6. The method of any one of paragraphs 1 to 4, wherein the hydrocarbon feed contains ≥1.0 wt % aromatic carbon based on the weight of the hydrocarbon feed and wherein the contacting is conducted under conversion conditions to convert ≤20.0 wt % of the aromatic carbon based on the weight of the hydrocarbon feed is converted to non-aromatic carbon.

7. The method of paragraph 6, wherein (i) the conversion is operated to convert at least a portion of the resid and (ii) the amount of aromatic carbon converted is ≤0.25 times the amount of resid converted; the amounts being based on the weight of the hydrocarbon feed 8. The method of claim 6, wherein the contacting is conducted under conversion conditions to convert the aromatic carbon to aliphatic carbon, wherein the amount of aromatic carbon converted is ≤0.5 times the amount of resid converted, the amounts being based on the weight of the hydrocarbon feed.

9. The method of paragraph 6, wherein the amount of aromatic carbon converted to aliphatic carbon is ≤0.25 times the amount of resid converted, the amounts being based on the weight of the hydrocarbon feed.

10. The method of any one of paragraphs 1 to 9, wherein the hydrocarbon feed comprises 20.0 wt % resid based on the weight of the hydrocarbon feed.

11. The method of any one of paragraphs 1 to 10, wherein the hydrocarbon feed comprises ≥30.0 wt % resid based on the weight of the hydrocarbon feed.

12. The method of any one of paragraphs 1 to 11, wherein the hydrocarbon feed has a hydrogen content ≤about 13 wt % based on the weight of the hydrocarbon in the hydrocarbon feed.

13. The method of any of paragraphs 1 to 12, wherein the reactor product has a $C_{3+}$ to $C_2$ unsaturate weight ratio ≤0.5 and comprises ≥20.0 wt % acetylene, the acetylene being derived from the converted hydroprocessed product, and wherein the high-severity operating conditions include a pressure ≥36 pounds per square inch gauge (248 kilo Pascal).

14. The method of any one of paragraphs 1 to 13, wherein the reactor product has an ethylene to acetylene weight ratio ≥0.1.

15. The method of any one of paragraphs 1 to 14, wherein the pyrolysis feed further comprises hydrogen ($H_2$) added to at least a portion of the hydroprocessed product, wherein the pyrolysis feed has a hydrogen ($H_2$) to carbon (in hydrocarbon) molar ratio is in the range of 0.1:5 to 1:1.

16. The method of any one of paragraphs 1 to 15, further comprising converting at least a portion of the reactor product into ethylene.

17. The method of paragraph 16, further comprising polymerizing at least a portion of the ethylene.

18. The method of paragraph 16 or 17, further comprising separating hydrogen ($H_2$) from at least a portion of the reactor product.

19. The method of any one of paragraphs 16 to 18, further comprising separating the hydrogen ($H_2$) downstream of the ethylene converting.

20. The method of paragraph 18 or 19, wherein the hydrogen separation is carried out via one or more of a hydrogen membrane, pressure swing adsorption, electrochemical, cryogenic separation or solvent absorption.

21. The method of paragraph 18 or 19, further comprising adding a portion of the separated hydrogen ($H_2$) to the at least a portion of the hydroprocessed product.

22. The method of any one of paragraphs 1 to 21, wherein the at least a portion of the hydroprocessed product is exposed to peak pyrolysis gas temperature in the range of 1540.0° C. to 2200.0° C. for a residence time in the range of 0.5 seconds to 0.001 seconds.

23. The method of any one of paragraphs 1 to 21, wherein the at least a portion of the hydroprocessed product feed is exposed to peak pyrolysis gas temperature in the range of 1600.0° C. to 1800.0° C. for a residence time in the range of 0.5 second to 0.001 second.

24. The method of any one of paragraphs 1 to 23, further comprising: exothermically reacting a first combustion feed with a second combustion feed to heat a region at least partially within a thermal pyrolysis reactor; removing combustion products from the thermal pyrolysis reactor; and heating the pyrolysis feed using at least a portion of the heat generated by the exothermic reaction.

25. The method of paragraph 24, further comprising purging the heated region with a vapor purge stream after the removing the combustion products and prior to passing the at least a portion of the pyrolysis feed into the heated region.

26. The method of paragraph 24 or 25, wherein the combustion and pyrolysis in the thermal pyrolysis reactor are conducted in sequence, the sequence having a cycle time in the range of 0.5 seconds to 30 seconds.

27. The method of paragraph 24 or 25, wherein the first combustion feed and the second combustion feed are separately heated within the thermal pyrolysis reactor prior to exothermically reacting in the region.

28. The method of any one of paragraphs 1 to 26, further comprising separating from the hydroprocessed product the pyrolysis feed and a bottoms product.

29. The method of any one of paragraphs 1 to 28, further comprising: separating from a second hydrocarbon feed a second pyrolysis feed and the first hydrocarbon feed; exposing the second pyrolysis feed in a second pyrolysis reactor to pyrolysis conditions to produce a second reactor product; and combining at least a portion of the second reactor product with at least a portion of the reactor product.

30. An apparatus for processing hydrocarbons comprising: a hydroprocessing unit configured to contact hydrogen ($H_2$) and a hydrocarbon feed containing ≥10 wt % resid in the hydrocarbon feed with a catalyst to form a hydroprocessed product; a feed separation unit in fluid communication with the hydroprocessing unit and configured to receive the hydroprocessed product and separate a bottoms product from the hydroprocessed product; a thermal pyrolysis reactor in fluid communication with the feed separation unit configured to expose a pyrolysis feed derived from the hydroprocessed product at high-severity thermal pyrolysis operating conditions to produce a reactor product that comprises ethylene and acetylene; and a product separation unit in fluid communication with the thermal pyrolysis reactor and configured to separate hydrogen from at least a portion of the reactor product.

31. The apparatus of paragraph 30, further comprising a converter in fluid communication with the thermal pyrolysis reactor, the converter being configured to convert at least a portion of the reactor product into ethylene.

32. The apparatus of paragraph 31, further comprising a polymerization unit in fluid communication with the converter, the polymerization unit being configured to convert at least a portion of the conversion product into polyethylene.

33. The apparatus of any one of paragraphs 30 to 32, wherein the product separation unit is in fluid communication between the converter and the thermal pyrolysis unit, these being configured to provide the separated hydrogen to the hydroprocessing unit.

34. The apparatus of any one of paragraphs 30 to 33, further comprising a conversion product separation unit in fluid communication with the converter, the conversion product separation unit being configured to separate hydrogen from the product from the converter.

35. The apparatus of any one of paragraphs 33 to 34, wherein the product separation unit comprises one or more of a hydrogen membrane, a pressure swing adsorption unit, an electrochemical unit, a cryogenic separation unit and a solvent absorption unit.

36. The apparatus of any one of paragraphs 30 to 35, wherein the thermal pyrolysis reactor is configured to expose the pyrolysis feed to peak pyrolysis gas temperature from 1540.0° C. to 2200.0° C., and maintain the at least a portion of the pyrolysis feed within the thermal pyrolysis reactor for a residence time in the range of 0.5 seconds to 0.001 seconds.

37. The apparatus of any one of paragraphs 30 to 35, wherein the thermal pyrolysis reactor is configured to expose the pyrolysis feed to peak pyrolysis gas temperature from 1600.0° C. to 1800.0° C., and maintain the at least a portion of the pyrolysis feed within the thermal pyrolysis reactor for a residence time in the range of 0.5 seconds to 0.001 seconds.

38. The apparatus of any one of paragraphs 30 to 37, wherein the thermal pyrolysis reactor is a regenerative reverse flow reactor that comprises: a reactor body, wherein the reactor body forms a reaction region within the reactor body; a packing material disposed at least partially within the reaction region; and one or more valve assemblies coupled to the reactor body and in flow communication with the reaction region and configured to control fluid flow of the at least a portion of the hydroprocessed product between a location external to the reactor body and within the reaction region.

39. The apparatus of paragraph 38, wherein the one or more valve assemblies comprise one or more poppet valve assemblies.

40. The apparatus of any one of paragraphs 30 to 39, further comprising: a second pyrolysis reactor configured to expose a second pyrolysis feed within the second pyrolysis reactor to pyrolysis conditions to produce a second reactor product comprising ethylene and acetylene; and a primary feed separation unit in fluid communication with the hydroprocessing unit and the second pyrolysis reactor and configured to separate a feed into the hydrocarbon feed and a second pyrolysis feed.

41. The apparatus of paragraph 40, further comprising a combining unit configured to combine at least a portion of the reactor product with at least a portion of the second reactor product prior the converter.

42. The apparatus of any one of paragraphs 30 to 40, further comprising a gasification unit in fluid communication with the hydroprocessing unit, the gasification unit being configured to convert a biological matter into a vapor fraction and a liquid fraction, wherein the hydrocarbon feed is derived from the liquid fraction.

43. The method of any of paragraphs 1 to 29, further comprising gasifying biological matter to produce a vapor fraction and a liquid fraction, wherein the hydrocarbon feed is derived from the liquid fraction.

44. The method of paragraph 43, wherein the pyrolysis feed comprises hydrocarbons that contain one or more heteroatoms that comprise ≥10 atom % of the atoms present in hydrocarbons.

While the present invention has been described and illustrated with respect to certain embodiments, it is to be understood that the invention is not limited to the particulars disclosed and extends to all equivalents within the scope of the claims.

The invention claimed is:

1. A method for processing hydrocarbons comprising: contacting molecular hydrogen and a hydrocarbon feed containing ≥10.0 wt % resid in the hydrocarbon feed with a catalyst under catalytic hydrotreating conditions to form a hydroprocessed product; deriving a pyrolysis feed from the hydroprocessed product, and exposing the pyrolysis feed at high-severity thermal pyrolysis operating conditions in a regenerative reverse-flow thermal pyrolysis reactor to produce a reactor product that comprises molecular hydrogen, ethylene and acetylene; and separating at least a portion of the molecular hydrogen from the reactor product, wherein (i) the molecular hydrogen contacting the catalyst comprises at least a portion of the separated molecular hydrogen, (ii) the catalytic hydrotreating conditions include a molecular hydrogen partial pressure which substantially avoids aromatic saturation of the hydrocarbon feed, (iii) the high-severity thermal pyrolysis operating conditions include a temperature ≥1540.0° C., a residence time in the range of from 4 milliseconds to 50 milliseconds, and a pressure ≥44 psig, and (iv) the reactor product has a $C_{3+}$ to acetylene weight ratio in the range of from 0.261 to 0.5.

2. The method of claim 1, wherein the reactor product has a $C_{3+}$ to acetylene weight ratio ≤0.45.

3. The method of claim 1, wherein ≥20.0 wt % of the resid is converted to components having a normal boiling point ≤565° C.

4. The method of claim 1, further comprising removing combustible non-volatiles, non-combustible non-volatiles or combinations thereof from the hydroprocessed product, the hydroprocessed product comprising ≤5.0 wt % of the combustible non-volatiles and ≤2 ppmw of the non-combustible non-volatiles based on the weight of the hydroprocessed product.

5. The method of claim 1, wherein the hydrocarbon feed contains ≥1.0 wt % aromatic carbon based on the weight of the hydrocarbon feed and wherein the contacting is conducted under conversion conditions to convert ≤20.0 wt % of the aromatic carbon based on the weight of the hydrocarbon feed to non-aromatic carbon.

6. The method of claim 5, wherein (i) the conversion is operated to convert at least a portion of the resid and (ii) the amount of aromatic carbon converted is ≤0.25 times the amount of resid converted; the amounts being based on the weight of the hydrocarbon feed.

7. The method of claim 1, wherein the hydrocarbon feed comprises ≥20.0 wt % resid based on the weight of the hydrocarbon feed.

8. The method of claim 1, wherein the hydrocarbon feed has a hydrogen content ≤about 13 wt % based on the weight of the hydrocarbon in the hydrocarbon feed.

9. The method of claim 1, wherein the reactor product has a $C_{3+}$ to $C_2$ unsaturate weight ratio ≤0.5 and comprises ≥20.0 wt % acetylene, the acetylene being derived from the hydroprocessed product, and wherein the high-severity thermal pyrolysis operating conditions include a pressure ≥103 psig.

10. The method of claim 1, wherein the pyrolysis feed further comprises molecular hydrogen added to at least a portion of the hydroprocessed product, wherein the pyrolysis feed has a molar ratio of hydrogen to carbon atoms in the hydroprocessed product in the range of 0.02:1 to 1:1.

11. The method of claim 1, further comprising converting at least a portion of the reactor product into ethylene.

12. The method of claim 11, further comprising polymerizing at least a portion of the ethylene.

13. The method of claim 11, further comprising separating molecular hydrogen from at least a portion of the reactor product, and adding a portion of the separated molecular hydrogen to the hydroprocessed product.

14. The method of claim 1, further comprising separating from the hydroprocessed product the pyrolysis feed and a bottoms product.

15. The method of claim 1, wherein the catalytic hydrotreating conditions include a hydrogen consumption rate of about 200 scf/bbl to about 2000 scf/bbl.

16. The method of claim 1, wherein the reactor product has an ethylene to acetylene weight ratio of about 0.1 to about 0.5.

\* \* \* \* \*